(12) United States Patent
Huang et al.

(10) Patent No.: US 10,108,777 B2
(45) Date of Patent: Oct. 23, 2018

(54) METHODS FOR IDENTIFYING DNA COPY NUMBER CHANGES

(75) Inventors: Jing Huang, Sunnyvale, CA (US);
Keith W. Jones, Sunnyvale, CA (US);
Michael H. Shapero, Sunnyvale, CA (US)

(73) Assignee: Affymetrix, Inc., Carlsbad, CA (US)

( * ) Notice: Subject to any disclaimer, the term of this patent is extended or adjusted under 35 U.S.C. 154(b) by 0 days.

(21) Appl. No.: 13/459,603

(22) Filed: Apr. 30, 2012

(65) Prior Publication Data

US 2012/0214704 A1 Aug. 23, 2012

Related U.S. Application Data

(60) Continuation of application No. 12/902,711, filed on Oct. 12, 2010, now Pat. No. 8,190,373, which is a division of application No. 11/295,225, filed on Dec. 5, 2005, now Pat. No. 7,822,555, which is a continuation-in-part of application No. 11/044,831, filed on Jan. 26, 2005, now abandoned, which is a
(Continued)

(51) Int. Cl.
| | |
|---|---|
| *G06F 19/00* | (2018.01) |
| *G06F 19/18* | (2011.01) |
| *C12Q 1/6827* | (2018.01) |
| *C12Q 1/6837* | (2018.01) |
| *G06F 19/20* | (2011.01) |

(52) U.S. Cl.
CPC ........... *G06F 19/18* (2013.01); *C12Q 1/6827* (2013.01); *C12Q 1/6837* (2013.01); *G06F 19/20* (2013.01)

(58) Field of Classification Search
CPC .......... G06F 19/00; G06F 19/20; G06F 19/24; G06F 19/12; G06F 19/18; G06F 19/22; G06F 19/26; G06F 19/10; G06F 19/16; G06F 19/325; G16H 50/20
See application file for complete search history.

(56) References Cited

U.S. PATENT DOCUMENTS

| | | |
|---|---|---|
| 5,427,932 A | 6/1995 | Weier |
| 5,447,841 A | 9/1995 | Gray |
| | (Continued) | |

FOREIGN PATENT DOCUMENTS

| | | |
|---|---|---|
| WO | WO 1997/10365 | 3/1997 |
| WO | WO 1999/23256 | 5/1999 |
| WO | WO 2004/058945 | 7/2004 |

OTHER PUBLICATIONS

Mei. R. Genome Research 2000 vol. 10 p. 1126-1137.*
(Continued)

*Primary Examiner* — Mary K Zeman
(74) *Attorney, Agent, or Firm* — Mauriel Kapouytian Woods LLP; Elaine K. Lee; Michael Mauriel

(57) ABSTRACT

Methods of identifying allele-specific changes in genomic DNA copy number are disclosed. Methods for identifying homozygous deletions and genetic amplifications are disclosed. An array of probes designed to detect presence or absence of a plurality of different sequences is also disclosed. The probes are designed to hybridize to sequences that are predicted to be present in a reduced complexity sample. The methods may be used to detect copy number changes in cancerous tissue compared to normal tissue. The methods may be used to diagnose cancer and other diseases associated with chromosomal anomalies.

14 Claims, 6 Drawing Sheets

Related U.S. Application Data continuation of application No. 10/913,928, filed on Aug. 6, 2004, now abandoned, which is a continuation of application No. 10/712,616, filed on Nov. 12, 2003, now Pat. No. 7,424,368.

(60) Provisional application No. 60/633,179, filed on Dec. 3, 2004, provisional application No. 60/694,102, filed on Jun. 24, 2005, provisional application No. 60/319,685, filed on Nov. 11, 2002, provisional application No. 60/319,750, filed on Dec. 3, 2002, provisional application No. 60/467,105, filed on Apr. 30, 2003.

(56) References Cited

U.S. PATENT DOCUMENTS

| | | |
|---|---|---|
| 5,472,842 A | 12/1995 | Stokke |
| 5,633,365 A | 5/1997 | Stokke |
| 5,665,549 A | 9/1997 | Pinkel et al. |
| 5,721,098 A | 2/1998 | Pinkel |
| 5,801,021 A | 9/1998 | Gray |
| 5,830,645 A | 11/1998 | Pinkel |
| 5,840,482 A | 11/1998 | Gray |
| 5,856,097 A | 1/1999 | Pinkel et al. |
| 5,965,362 A | 10/1999 | Pinkel et al. |
| 5,976,790 A | 11/1999 | Pinkel et al. |
| 6,159,685 A | 12/2000 | Pinkel |
| 6,180,349 B1 | 1/2001 | Ginzinger et al. |
| 6,261,770 B1 | 7/2001 | Warthoe |
| 6,261,775 B1 | 7/2001 | Bastian |
| 6,268,142 B1 | 7/2001 | Duff |
| 6,268,184 B1 | 7/2001 | Gray |
| 6,277,563 B1 | 8/2001 | Shayesteh |
| 6,280,929 B1 | 8/2001 | Gray |
| 6,309,822 B1 | 10/2001 | Fodor et al. |
| 6,326,148 B1 | 12/2001 | Pauletti et al. |
| 6,335,167 B1 | 1/2002 | Pinkel et al. |
| 6,344,316 B1 | 2/2002 | Lockhart et al. |
| 6,358,683 B1 | 3/2002 | Collins |
| 6,365,353 B1 | 4/2002 | Lorch |
| 6,432,648 B1 | 8/2002 | Blumenfeld |
| 6,444,426 B1 | 9/2002 | Short |
| 6,451,529 B1 | 9/2002 | Jensen |
| 6,455,258 B2 | 9/2002 | Bastian et al. |
| 6,455,280 B1 | 9/2002 | Edwards |
| 6,465,180 B1 | 10/2002 | Bastian |
| 6,465,182 B1 | 10/2002 | Gray |
| 6,468,744 B1 | 10/2002 | Cronin et al. |
| 6,475,732 B1 | 11/2002 | Shayesteh |
| 6,500,612 B1 | 12/2002 | Gray |
| 6,562,565 B1 | 5/2003 | Pinkel |
| 6,596,479 B1 | 7/2003 | Gray |
| 6,617,137 B2 | 9/2003 | Dean |
| 6,664,057 B2 | 12/2003 | Albertson |
| 2001/0034023 A1 | 10/2001 | Stanton et al. |
| 2002/0165345 A1 | 7/2002 | Cohen |
| 2003/0009292 A1* | 1/2003 | Mei .................. G06F 19/18 702/19 |
| 2004/0137473 A1 | 7/2004 | Wigler et al. |

OTHER PUBLICATIONS

Buckley et al., A Full-coverage, High-resolution Human Chromosome 22 Genomic Mircroarray for Clinical and Research Applications. Human Molecular Genetics, 2002, 3221-3229, vol. 11(5).
Draghici; Drug Discovery Today, vol. 7, pp. S55-S63, Jun. 2002.
Dumur et al., Genome-wide Detection of LOH in Prostate Cancer Using Human SNP Microarray Technology. Genomics, 2003, 260-269, vol. 81.
Huang et al; Genome Research 2004, 194) 287-299.
Kallioniemi et al., Comparative Genomic Hybridization: A Powerful New Method for Cytogenetic Analysis of Solid Tumors. Science, 1992, 818-821, vol. 258.
Kaminski et al; American Journal of Respiratory Cell and Molecular Biology, vol. 27, pp. 125-132, Aug. 2002.
Kennedy et. al., Large-scale Genotyping of Complex Dna. Nature Biotechnology, Oct. 2003, 1233-1237, vol. 21 (10).
Klein et al., Comparative Genomic Hybridization, Loss of Heterozygosity, and DNA Sequence Analysis of Single Cells, Proc Natl Acad Sci, 1999, 4494-4499, vol. 96.
Laan, et al., Solid-phase minisequencing confirmed by FISH analysis in determination of gene copy number, Human Genetics, 96(3), 275-80, 1995.
Lindblad-Toh et al., Loss of Heterozygosity Analysis of Small Cell Lung Carcinomas Using Single-Nucleotide Polymorphism Arrays. Nature Biotechnology, Sep. 2000, 1001-1005, vol. 18.
Lucito et al., Detecting Gene Copy Number Fluctuations in Tumor Cells by Microarray Analysis of Genomic Representations. Genome Research, 2000, 1726-1736, vol. 10(11).
Lucito et al., Genetic Analysis Using Genomic Representations. Proc Natl Acad Sci, Apr. 1998, 4487-4492, vol. 95.
Lucito et al., Representational Oligonucleotide Microarray Analysis: A High-Resolution Method to Detect Genome Copy Number Variation. Genome Research, 2003, 2291-2305, vol. 13 (10).
Mei et al., Genome-wide Detection of Allelic Imbalance Using Human SNPs and High-density DNA Arrays. Genome Research. 2000, 1126-1137, vol. 10 (8).
Mohapatra et al; Analyses of Brain Tumor Cell Lines Comfirm a Simple Model of Relationships Among Fluorescence In Situ Hybridization, DNA Index, and Comparative Genomic Hybridization, 1997, Genes, Chromosomes, and Cancer; vol. 20, pp. 311-319.
Paez et al., Genome coverage and sequence fidenify of f29 polymerase-based multiple strand displacement whole genome apmplification, Nuc. Acids Research 32(9) e71 pp1-11.
Pinkel et al., High Resolution Analysis of DNA Copy Number Variation Using Comparative Genomic Hybridization to Microarrays. Nature Genetics, 1998, 207-211, vol. 20.
Pollack et al., Microarray Analysis Reveals a Major Direct Role of DNA Copy Number Alterations in the Transcriptional Program of Human Breast Tumors. Proc Natl Acad Sci, Oct. 2002, 12963-12968, vol. 99 (20).
Schubert et al., Single Nucleotide Polymorphism Array Analysis of Flow-Sorted Epithelial Cells from Frozen Versus Fixed Tissues for Whole Genome Analysis of Allelic Loss in Breast Cancer. Am J Pathol, 2002, 73-79, vol. 160.
Sebat et al., Large-Scale Copy Number Polymorphism in the Human Genome, Science vol. 305 p. 525-28.
Snijders et al., Assembly of Microarrays for Genome-wide Measurement of DNA Copy Number. Nature Genetics, 2001, 263-264, vol. 29.
Wodicka et al; Nature Biotechnology, 15, 1359-1367, 1997.
Zhou et al; BMC Bioinformatics, vol. 3, Jan. 2002.

* cited by examiner

PRIOR ART

METHODS FOR IDENTIFYING DNA COPY NUMBER CHANGES

RELATED APPLICATIONS

This application claims the priority of U.S. Provisional Applications No. 60/633,179 filed Dec. 3, 2004 and 60/694,102 filed Jun. 24, 2005 and is a continuation in part of U.S. patent application Ser. No. 11/044,831 which is a continuation-in-part of U.S. patent application Ser. No. 10/913,928, which is a continuation-in-part of U.S. patent application Ser. No. 10/712,616 which claims the priority of U.S. Provisional Application Nos. 60/319,685 filed Nov. 11, 2002, 60/319,750 filed Dec. 3, 2002 and 60/467,105 filed Apr. 30, 2003. The disclosures of each of the above applications are incorporated herein by reference in their entireties for all purposes.

FIELD OF THE INVENTION

The invention is related to methods of estimating the number of copies of a genomic region that are present in a sample. Specifically, this invention provides methods, computer software products and systems for the detection of regions of chromosomal amplification and deletion from a biological sample.

BACKGROUND OF THE INVENTION

The underlying progression of genetic events which transform a normal cell into a cancer cell is characterized by a shift from the diploid to anueploid state (Albertson et al. (2003), *Nat Genet*, Vol. 34, pp. 369-76 and Lengauer et al. (1998), *Nature*, Vol. 396, pp. 643-9). As a result of genomic instability, cancer cells accumulate both random and causal alterations at multiple levels from point mutations to whole-chromosome aberrations. DNA copy number changes include, but are not limited to, loss of heterozygosity (LOH) and homozygous deletions, which can result in the loss of tumor suppressor genes, and gene amplification events, which can result in cellular proto-oncogene activation. One of the continuing challenges to unraveling the complex karyotype of the tumor cell is the development of improved molecular methods that can globally catalogue LOH, gains, and losses with both high resolution and accuracy.

Numerous molecular approaches have been described to identify genome-wide LOH and copy number changes within tumors. Classical LOH studies designed to identify allelic loss using paired tumor and blood samples have made use of restriction fragment length polymorphisms (RFLP) and, more often, highly polymorphic microsatellite markers (STRS, VNTRs). The demonstration of Knudson's two-hit tumorigenesis model using LOH analysis of the retinoblastoma gene, Rbl, showed that the mutant allele copy number can vary from one to three copies as the result of biologically distinct second-hit mechanisms (Cavenee, et al. (1983), *Nature*, Vol. 305, pp. 779-84.). Thus regions undergoing LOH do not necessarily contain DNA copy number changes.

Approaches to measure genome wide increases or decreases in DNA copy number include comparative genomic hybridization (CGH) (Kallioniemi, et al. (1992), *Science*, Vol. 258, pp. 818-21.), spectral karyotyping (SKY) (Schrock, et al. (1996), *Science*, Vol. 273, pp. 494-7.), fluorescence in situ hybridization (FISH) (Pinkel et al. (1988), *Proc Natl Acad Sci USA*, Vol. 85, pp. 9138-42) molecular subtraction methods, such as RDA (Lisitsyn et al. (1995), *Proc Natl Acad Sci USA*, Vol. 92, pp. 151-5.; Lucito et al. (1998), *Proc Natl Acad Sci USA*, Vol. 95, pp. 4487-92), and digital karyotyping (Wang, et al. (2002), *Proc Natl Acad Sci USA*, Vol. 99, pp. 16156-61.). CGH, perhaps the most widely used approach, uses a mixture of DNA from normal and tumor cells that have been differentially labeled with fluorescent dyes. Target DNA is competitively hybridized to metaphase chromosomes or, in array CGH, to cDNA clones (Pollack et al. (2002), *Proc Natl Acad Sci USA*, Vol. 99, pp. 12963-8) or bacterial artificial chromosomes (BACs) and P1 artificial chromosomes (PACs) (Snijders et al. (2001), *Nat Genet*, Vol. 29, pp. 263-4, Pinkel, et al. (1998), *Nat Genet*, Vol. 20, pp. 207-11). Hybridization to metaphase chromosomes, however, limits the resolution to 10-20 Mb, precluding the detection of small gains and losses. While the use of arrayed cDNA clones allows analysis of transcriptionally active regions of the genome, the hybridization kinetics may not be as uniform as when using large genomic clones. Currently, the availability of BAC clones spanning the genome limits the resolution of CGH to 1-2 Mb. CGH, however, is not well-suited to identify regions of the genome which have undergone LOH such that a single allele is present but there is no reduction in copy number.

With the completion of the human genome, single nucleotide polymorphisms (SNPs), the most common sequence variation among individuals, are emerging as the marker of choice in large-scale genetic studies due to their abundance, stability, and relative ease of scoring. These same characteristics make SNPs powerful markers for LOH studies.

SUMMARY OF THE INVENTION

Methods of estimating copy number using high density arrays of probes that are allele specific probes to single nucleotide polymorphisms are disclosed. Algorithms and computer software programs that direct computer hardware to perform the steps of the method are also disclosed. Probe intensity information is used to infer copy number in an allele-specific manner. Probe intensities are normalized using probe intensity measurements from references samples that are matched in genotype at particular polymorphic positions. Individual probes for each SNP are tested for the ability to support allelic dosage response using a set of normal individuals.

BRIEF DESCRIPTION OF THE DRAWINGS

The accompanying drawings, which are incorporated in and form a part of this specification, illustrate embodiments of the invention and, together with the description, serve to explain the principles of the invention.

Figure 1:
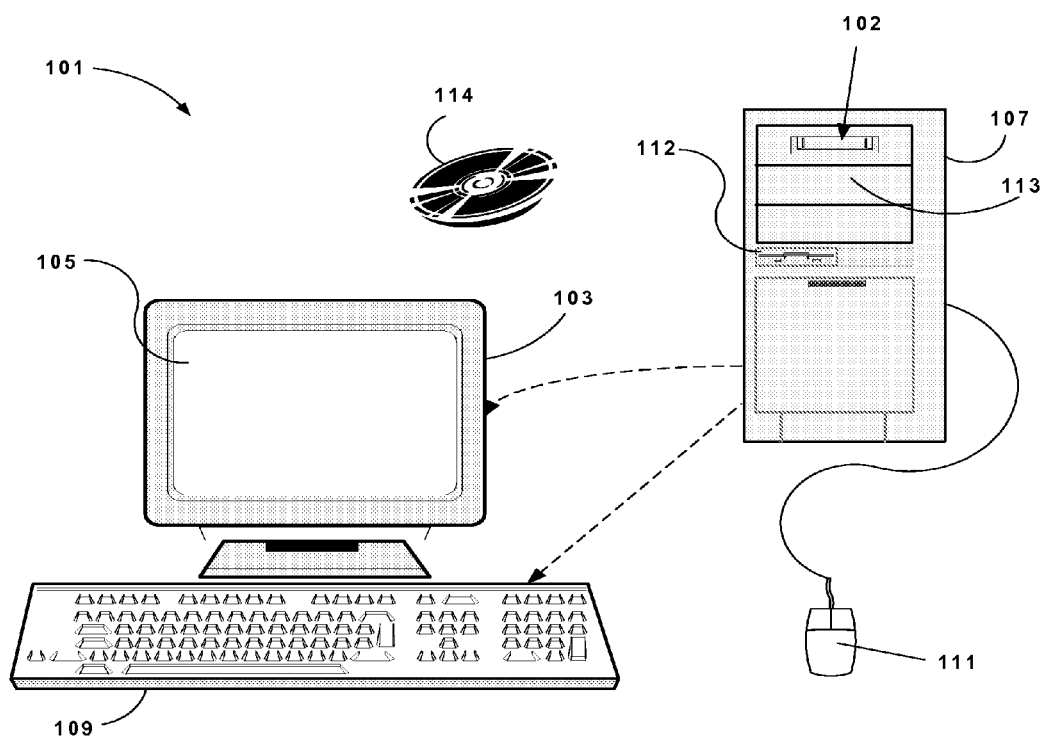
FIG. 1 illustrates an example of a computer system that may be utilized to execute the software of an embodiment of the invention.

DETAILED DESCRIPTION OF THE INVENTION (A) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. All references to the function log default to e as the base (natural log) unless stated otherwise (such as $\log_{10}$).

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (*Vols. I-IV*), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, "*Oligonucleotide Synthesis: A Practical Approach*" 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No 6,300,070 and U.S. patent application Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al. 1992, Nucleic Acids Res. 20(7):1691-6, 1992, and rolling circle amplification, described in U.S. Pat. No. 5,648,245. Other amplification methods that may be used are described in, U.S. Pat.

Nos. 5,242,794, 5,494,810, 4,988,617 and in U.S. Ser. No. 09/854,317 and US Pub. No. 20030143599, each of which is incorporated herein by reference. In some embodiments DNA is amplified by multiplex locus-specific PCR. In a preferred embodiment the DNA is amplified using adaptor-ligation and single primer PCR. Other available methods of amplification, such as balanced PCR (Makrigiorgos, et al. (2002), *Nat Biotechnol*, Vol. 20, pp. 936-9), may also be used.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, Bioinformatics Basics: Application in *Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654.

Additionally, the present invention may have preferred embodiments that include methods for providing genetic information over networks such as the Internet as shown in U.S. patent application Ser. Nos. 10/063,559, 60/349,546, 60/376,003, 60/394,574, 60/403,381.

(B) Definitions

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry, at* 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An oligonucleotide or polynucleotide is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term fragment refers to a portion of a larger DNA polynucleotide or DNA. A polynucleotide, for example, can be broken up, or fragmented into, a plurality of fragments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," $3^{rd}$ Ed. Cold Spring Harbor Laboratory Press, Cold Spring Harbor, N.Y. (2001) ("Sambrook et al.") which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

"Genome" designates or denotes the complete, single-copy set of genetic instructions for an organism as coded into the DNA of the organism. A genome may be multi-chromosomal such that the DNA is cellularly distributed among a plurality of individual chromosomes. For example, in human there are 22 pairs of chromosomes plus a gender associated XX or XY pair.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ by while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

The term subset or representative subset refers to a fraction of a genome. The subset may be 0.1, 1, 3, 5, 10, 25, 50 or 75% of the genome. The partitioning of fragments into subsets may be done according to a variety of physical characteristics of individual fragments. For example, fragments may be divided into subsets according to size, according to the particular combination of restriction sites at the ends of the fragment, or based on the presence or absence of one or more particular sequences.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., *Science*, 251:767-777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as optical fibers, glass or any other appropriate substrate. (See U.S. Pat. Nos. 5,770,358, 5,789,162, 5,708,153, 6,040,193 and 5,800,992, which are hereby incorporated by reference in their entirety for all purposes.)

Preferred arrays are commercially available from Affymetrix under the brand name GENECHIP® and are directed to a variety of purposes, including genotyping and gene expression monitoring for a variety of eukaryotic and prokaryotic species. (See Affymetrix Inc., Santa Clara and their website at affymetrix.com.) Methods for preparing sample for hybridization to an array and conditions for hybridization are disclosed in the manuals provided with the arrays, for example, for expression arrays the GENECHIP® Expression Analysis Technical Manual (PN 701021 Rev. 5) provides detailed instructions for 3' based assays and the GeneChip® Whole Transcript (WT) Sense Target Labeling Assay Manual (PN 701880 Rev. 2) provides whole transcript based assays. The GeneChip Mapping 100K Assay Manual (PN 701694 Rev. 3) provides detailed instructions for sample preparation, hybridization and analysis using genotyping arrays. Each of these manuals is incorporated herein by reference in its entirety.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

Polymorphism refers to the occurrence of two or more genetically determined alternative sequences or alleles in a population. A polymorphic marker or site is the locus at which divergence occurs. Preferred markers have at least two alleles, each occurring at frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens. Single nucleotide polymorphisms (SNPs) are positions at which two alternative bases occur at appreciable frequency (>1%) in the human population, and are the most common type of human genetic variation.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur at equal frequency, and linked locus Y has alleles c and d, which occur at equal frequency, one would expect the combination ac to occur at a frequency of 0.25. If ac occurs more frequently, then alleles a and c are in linkage disequilibrium. Linkage disequilibrium may result, for example, because the regions are physically close, from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

Normal cells that are heterozygous at one or more loci may give rise to tumor cells that are homozygous at those loci. This loss of heterozygosity may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene.

A homozygous deletion is a deletion of both copies of a gene or of a genomic region. Diploid organisms generally have two copies of each autosomal chromosome and therefore have two copies of any selected genomic region. If both copies of a genomic region are absent the cell or sample has a homozygous deletion of that region. Similarly, a hemizygous deletion is a deletion of one copy of a gene or of a genomic region.

Genetic rearrangement occurs when errors occur in DNA replication and cross over occurs between nonhomologous regions resulting in genetic material moving from one chromosomal location to another. Rearrangement may result in altered expression of the genes near the rearrangement.

An aneuploid is a cell whose chromosomal constitution has changed from the true diploid, for example, extra copies of a chromosome or chromosomal region.

An individual is not limited to a human being, but may also include other organisms including but not limited to mammals, plants, bacteria or cells derived from any of the above.

The Whole Genome Sampling Assay (WGSA) reduces the complexity of a nucleic acid sample by amplifying a subset of the fragments in the sample. A nucleic acid sample is fragmented with one or more restriction enzymes and an adapter is ligated to both ends of the fragments. A primer that is complementary to the adapter sequence is used to amplify the fragments using PCR. During PCR fragments of a selected size range are selectively amplified. The size range may be, for example, 400-800 or 400 to 2000 base pairs. Fragments that are outside the selected size range are not efficiently amplified.

The fragments that are amplified by WGSA may be predicted by in silico digestion and an array may be designed to genotype SNPs that are predicted to be amplified. Genotyping may be done by allele specific hybridization with probes that are perfectly complementary to individual alleles of a SNP. A set of probes that are complementary to the region surrounding each SNP may be present on the array. Perfect match probes are complementary to the target over the entire length of the probe. Mismatch probes are identical to PM probes except for a single mismatch base. The mismatch position is typically the central position so for a 25 base probe the mismatch is position 13.

The methods may be combined with other methods of genome analysis and complexity reduction. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592, 6,458,530 and U.S. Patent application Nos. 20030039069, 09/916,135, 09/920,491, 09/910,292 and 10/264,945, which are incorporated herein by reference in their entireties.

The design and use of allele-specific probes for analyzing polymorphisms is described by e.g., Saiki et al., *Nature* 324, 163-166 (1986); Dattagupta, EP 235,726, Saiki, and WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles.

A regression tree is a type of decision tree that deal with continuous variables. Regression trees are non-parametric models, an advantage of which is a high computational efficiency and a good compromise between comprehensibility and predictive accuracy. The regression tree method can be applied to very large datasets in which only a small proportion of the predictors are valuable for classification. See Breiman et al. *Classification and Regression Trees*, Wardsworth. 1984.

(C) Detection of Changes in Copy Number

Chromosome copy number analysis using whole-genome expression and genotyping microarray technology is fundamentally improving our understanding of human disease. The computerized methods and computer software products disclosed are particularly useful for analyzing the copy number of genomic regions using hybridization data obtained from high density genotyping or gene expression arrays. In particular the methods and computer software products will be described using exemplary embodiments in the context of copy number analysis using SNP genotyping arrays that allow genotyping of more than 10,000, more than 100,000 or more than 500,000 human SNPs using a single array or array set. In particular, the Affymetrix GeneChip® Human Mapping 10K, Mapping 100K Set or Mapping 500K Set in combination with the disclosed methods of analysis and software methods may be used to detect allele-specific copy number alterations, loss of heterozygosity (LOH), and genotypes in a single experiment.

Methods for determining copy number using high density SNP genotyping arrays using the Affymetrix 10K SNP genotyping array and the 100K Mapping Set are disclosed. The methods should also be useful for estimating copy number along with a higher density genotyping array, such as the 500K Mapping Set. The 10K array and the 100K array set use a WGSA target preparation scheme in which single primer PCR amplification of specific fractions of the genome is carried out. The 100K WGSA method uses two separate restriction enzymes that each generates a complexity fraction estimated to be about 300 Mb. The 10K array uses a single restriction enzyme and generates a sample with less than 300 Mb complexity. Both arrays have been shown to genotype SNPs, with call rates, reproducibility, and accuracy greater than 99%, 99.7%, and 99.7% respectively (Matsuzaki et al. *Nat Methods* 1: 109-111, 2004).

Genetic instability, such as changes in DNA copy number, is one of the hallmarks of many human cancers. High-density DNA array technology has been applied towards the identification of genomic alterations in tumor cells, most notably loss of heterozygosity (LOH) (Lindblad-Toh, et al. (2000), *Nat Biotechnol*, Vol. 18, pp. 1001-5, Mei, R., et al. (2000), *Genome Res*, Vol. 10, pp. 1126-37, Schubert, et al. (2002), *Am J Pathol*, Vol. 160, pp. 73-9, and Dumur et al. (2003), *Genomics*, Vol. 81, pp. 260-9). Methods are disclosed for using high density arrays for detection of LOH and genomic amplifications and deletions. In many embodiments the high density array is a genotyping array. However, other arrays of probes may be used, for example, an array of probes complementary to different regions of human genes, such as the Human Genome U133 Plus 2.0, available from Affymetrix, Inc, Santa Clara may be used. In general the methods compare the intensity of hybridization of nucleic acids to perfect match probes and correlate higher intensity with higher copy number. The relationship between log intensity and log copy number was found to be approximately linear and using control samples of known copy number the slope and y-intercept of the line may be estimated. Methods of genotyping many polymorphisms in parallel may be used to identify DNA gains and losses across multiple chromosomes. Methods that reduce complexity of a genomic sample in a predictable way can be used in combination with an array of probes designed to interrogate polymorphisms in the resulting reduced complexity genomic sample. Methods such as those disclosed in U.S. patent application Ser. No. 10/264,945 may be used to detect genotypes and the genotype information may be used to identify regions of homozygous deletion or regions of amplification. A single primer may be used to amplify representative fractions of the genome followed by SNP genotyping via hybridization to high density oligonucleotide arrays which comprise perfect match (PM) and mismatch (MM) probe sets from one or both strands of the DNA. Algorithms that use, for example, discrimination ratios between paired PM and MM intensity values may be used to identify regions of homozygous deletions or median PM intensities may be used to identify regions of gene amplification. Following chip intensity normalization, SNP discrimination ratios and PM intensities from an experimental sample may be compared to distributions derived from a references set containing normal individuals. In one embodiment the sample set contains over 10, 100, 400, 500, or 1,000 individuals, allowing statistically significant regions with DNA copy number changes to be identified. Additionally, statistically significant genomic intervals showing loss of heterozygosity (LOH) may be identified by calculating the likelkhood of a contiguous stretch of homozygous markers based on known allele frequencies. The SNPs are SNPs that are genotyped on the array being used and there may be SNPs in between the genotyped SNPs that are not genotyped. The allele frequencies may be obtained, for example, from a publicly available database, such as dbSNP, by genotyping a reference set of samples, or from any available database of allele frequencies. Using a data set derived from a single array, a sample can be analyzed for LOH, deletions, and amplifications. In one embodiment an array that has mean and median inter-SNP distances of about 250 kb and 120 kb respectively may be used. In another embodiment the mean and median inter-SNP distances are less than 100 kb and 20 kb respectively. This method may be used to detect copy number changes in any sample. In a preferred embodiment the tissue is a tissue that is suspected of being a cancerous tissue, for example, human breast cancer, prostate cancer, lung cancer and colon cancer.

Methods are disclosed for identifying chromosomal gains and losses at high resolution using high-density microarray genotyping methods such as whole genome sampling analysis (WGSA) (see, Kennedy et al. (2003), *Nat Biotechnol*, Vol., pp. 1233-1237, and U.S. patent application Ser. Nos. 09/920,492, 09/904,039, 10/681,773, 10/316,517, 10/442, 021, 10/463,991, 10/316, 629, and 10/264,945 and U.S. Pat. No. 6,361,947). WGSA simultaneously genotypes more than 10,000 SNPs in parallel by allele-specific hybridization to perfect match (PM) and mismatch (MM) probes synthesized on an array. Methods for chromosomal copy number analysis using the Affymetrix Mapping 10K array in combination with WGSA, have also been reported in Bignell et al. *Genome Res.* 14:287-295 (2004) and Huang et al., *Hum*

*Genomics* 1:287-299 (2004). Similar analysis using the Affymetrix Mapping 100K array has also been reported in Slater et al., *Am. J. Hum. Genet.* 77:709-726 (2005).

Novel algorithms that use probe intensity information to infer copy number in an allele-specific manner from high density DNA oligonuceotide arrays designed to genotype over 100,000 SNPs, are disclosed. Individual probes for each SNP are tested for the ability to support an allelic dosage response using a set of normal individuals. Total and allele-specific copy number estimations were independently evaluated for a subset of SNPs using quantitative PCR and TaqMan reactions with several human cancer cell lines. The sensitivity and specificity of the algorithm were characterized using DNA samples containing differing numbers of X chromosomes as well as a test set of normal individuals. The copy number algorithm allows for allele-specific output, and when coupled with SNP genotype calls from the same array, provides additional detail into the structure of genome wide alterations that contribute to allelic imbalance.

In one aspect of the invention, methods are provided for using SNP genotyping to identify allele based DNA copy number changes. SNP genotyping can be performed using a number of suitable methods, including genotyping arrays such as the 10K, 100K and 500K SNP arrays (Available from Affymetrix, Santa Clara, Calif.) using the Whole Genome Sampling Assay (WGSA) or other methods of amplification that may or may not involve complexity reduction. Arrays with larger numbers of SNPs may also be used along with any available method of genome amplification. The methods will be described using the Affymetrix 100K SNP array as examples. However, one of skill in the art would appreciate that the methods are not limited to the 100K SNP array. Any array that has allele specific perfect match probes that are complementary to regions of the genome may be used. FIG. 1 illustrates an example of a computer system that may be used to execute the software of an embodiment of the invention. FIG. 1 shows a computer system 101 that includes a display 103, screen 105, cabinet 107, keyboard 109, and mouse 111. Mouse 111 may have one or more buttons for interacting with a graphic user interface. Cabinet 107 houses a floppy drive 112, CD-ROM or DVD-ROM drive 102, system memory and a hard drive (113) (see also FIG. 2) which may be utilized to store and retrieve software programs incorporating computer code that implements the invention, data for use with the invention and the like. Although a CD 114 is shown as an exemplary computer readable medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
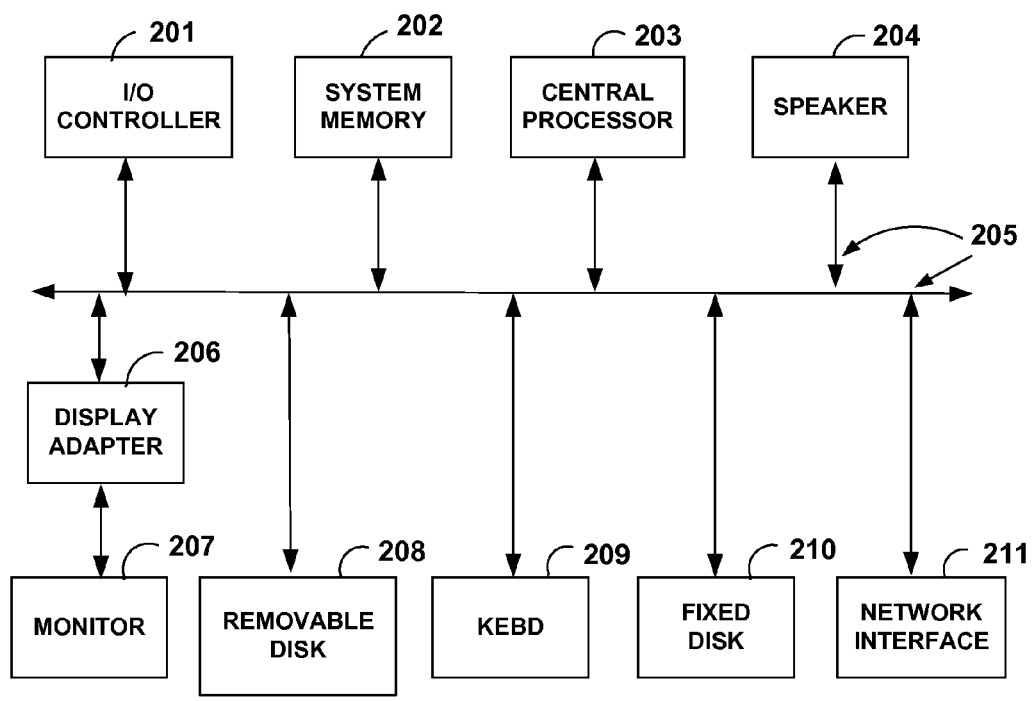
FIG. 2 illustrates a system block diagram of the computer system of FIG. 1.
Figure 3:
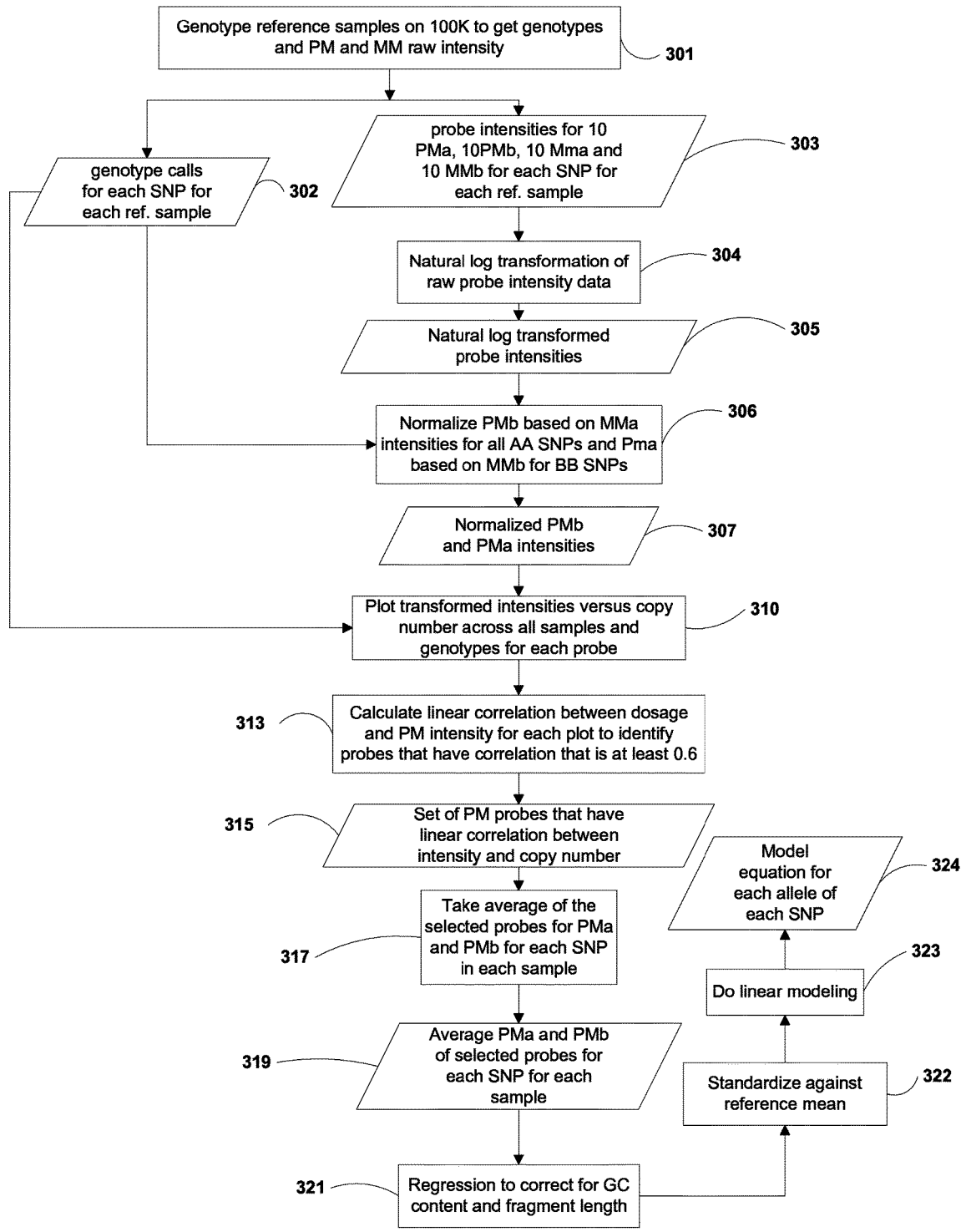
FIG. 3 shows a flowchart for a method of analyzing a set of reference samples to model equations for allele specific copy number analysis.
Figure 4:
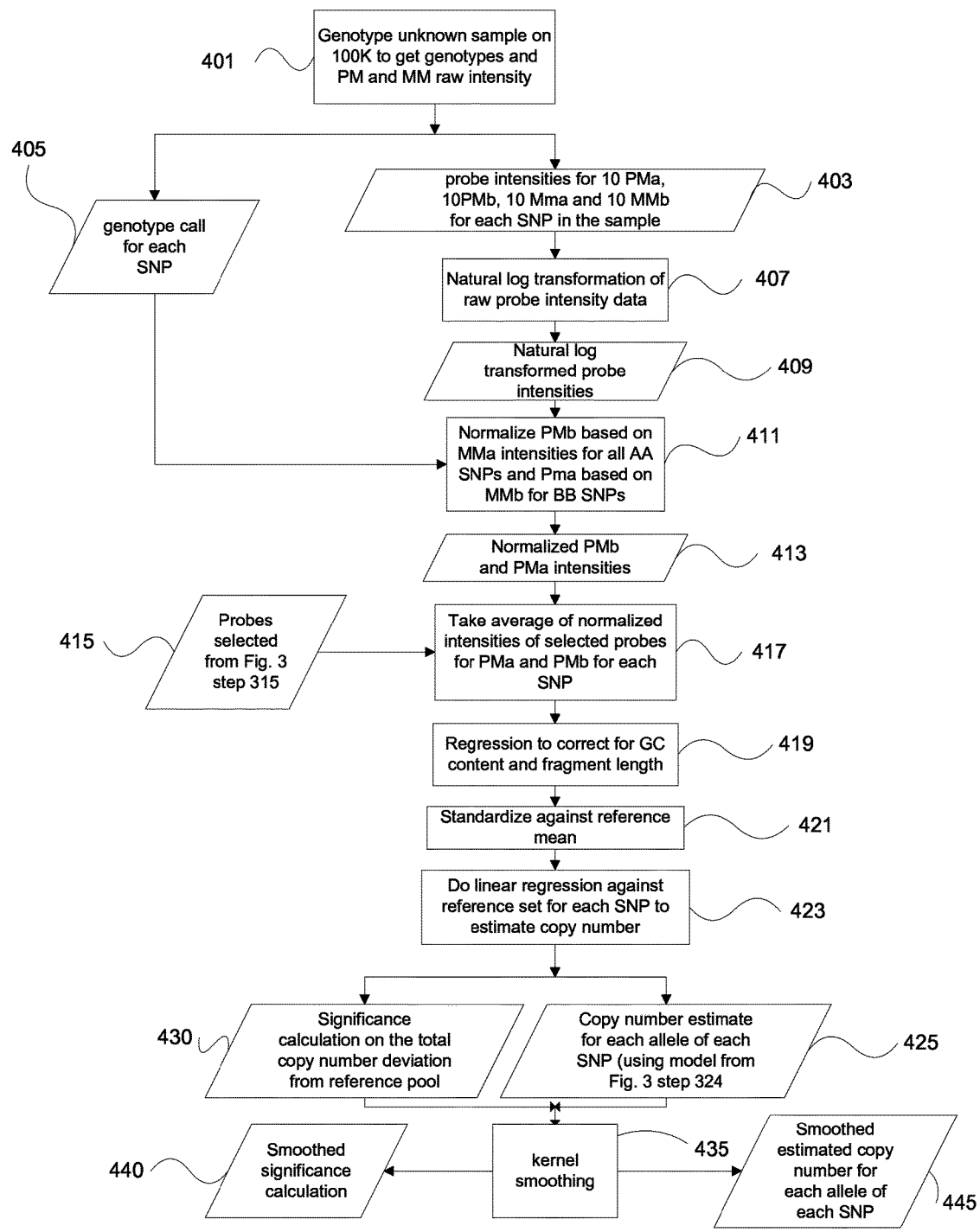
FIG. 4 shows a flowchart for a method of analyzing an unknown sample to estimate allele specific copy number using the modeled equations from FIG. 3.

FIG. 2 shows a system block diagram of computer system 101 used to execute the software of an embodiment of the invention. As in FIG. 1, computer system 101 includes monitor 201, and keyboard 209. Computer system 101 further includes subsystems such as a central processor 203 (such as a Pentium™ III processor from Intel), system memory 202, fixed storage 210 (e.g., hard drive), removable storage 208 (e.g., floppy or CD-ROM), display adapter 206, speakers 204, and network interface 211. Other computer systems suitable for use with the invention may include additional or fewer subsystems. For example, another computer system may include more than one processor 203 or a cache memory. Computer systems suitable for use with the invention may also be embedded in a measurement instrument. In a preferred aspect computer readable code In one embodiment the reference set may be, for example, more than 10, 100, 200, 300 or 500 normal individuals, allowing statistically significant regions to be identified. The method may be used with pure tumor samples or mixed samples, containing both normal and tumor DNA, but the methods may be used with any sample. In one embodiment the methods may be used to detect copy number changes in samples to determine if the sample is normal or has copy number changes. For example, the methods may be used for pre-natal diagnosis of diseases that correlate with amplification or deletion of genomic regions.

The methods disclose a molecular approach that may be used to identify within a single experiment regions of allelic loss along with regions of amplification that may lead to improved understanding of the cancer genome. The methods may be used to diagnose disease, for example cancer or diseases resulting from allelic imbalance. The methods may also be used to monitor treatment regimens to determine if a particular treatment results in changes in copy number of genomic regions.

In one embodiment genomic DNA is amplified directly without complexity reduction. One method for amplifying genomic DNA, Multiple Displacement Amplification (MDA), is described in Hosono S, et al. *Genome Res.* 13:954-64 (2003), Dean et al. *Proc Natl Acad Sci USA.* 16; 99(8):5261-6 (2002) and U.S. Pat. Nos. 6,617,137 and 6,642,034. MDA is an isothermal, strand-displacing amplification yielding about 20-30 um product from as few as 1-10 copies of human genomic DNA. Other methods of DNA amplification may also be used. Amplification can be carried out directly from biological samples including crude whole blood and tissue culture cells.

In one aspect control or reference samples that are identified as normal individuals are used to generate a model equation for each allele of each SNP to be analyzed. The reference samples may include more than 10, 50, 100, 200 or 500 individuals. Each reference sample is expected to have 2 copies of the majority of autosomal regions with an expected variation in allelic copy number between 0, 1 and 2. For example, if the individual is homozygous for the B allele they should have two copies of the B allele and 0 copies of the A allele. Heterozygotes should have 1 copy of each of the two alleles.

In one aspect of the present inventions a set of probe sets is identified from a genotyping array, such as the 100K array set, that show a near linear correlation (greater than 0.8) between the allelic copy number of the target and the observed intensity measurement of hybridization in a control sample set of normal individuals. The control individuals are assumed to have allelic copy number corresponding to the genotype of the SNP, for example an individual that is AA at SNP1 is assumed to have 2 copies of the A allele and 0 copies of the B allele. In this way a reference intensity set of 0, 1 and 2 copies of each allele of a plurality of SNPs is obtained.

A set of SNPs that shows a linear allele specific dose response is first identified using a reference sample. For each sample in the reference sample, WGSA is performed and the sample is genotyped on the 100K array to obtain a genotype call for each SNP (AA, BB, AB or no call) and probe intensities for each PM probe and each MM probe. The probe intensities are transformed to natural logs. Background intensity is defined for each sample as the MMa probe intensity for all SNPs with BB genotype and MMb probe intensity for all SNPs with AA genotype. All PMa probes are linearly transformed under the same transformation that when used to transform the MMa probe intensity for SNPs with BB genotype calls results in a mean of zero and a variance of one. All PMb probes are linearly transformed such that under the same transformation the MMb probe intensity for SNPs with AA genotype calls have a variance of one and a mean of zero. This step results in a set pf normalized PMa and PMb probe intensities for each sample.

The normalized PM intensities are then plotted versus copy number for each probe across all samples and genotypes, so 20 plots per SNP. Calculate a linear correlation for each probe between dosage conveyed by genotype and perfect match intensity. This provides a number between −1 and 1, with 1 being perfect linear correlation. Probes that have a linear correlation of at least 0.6 are kept. SNPs that have at least one PMa and PMb probe are kept. For those PMa and PMb probes that are kept calculate the average of the normalized intensity for the PMa or PMb for each SNP-this gives a PMa average for each SNP and a PMb average for each SNP in each sample. Standardize against reference mean. Optionally perform regression on GC content and fragment length. Do linear modeling to estimate allele specific copy number for each SNP, resulting in an A model and a B model for each SNP.

For the unknown sample genotype the SNPs identified in the steps above and make calls for each of these SNPs using WGSA and the 100K array. Perform natural log transformation of raw probe intensities. Normalize the transformed probe intensities using the mismatch probe intensities as above. Determine the average of the probes selected above for PMa or PMb for each SNP. Optionally do regression on GC content and fragment length. Correct systematic intensity deviations by regression on the reference set mean intensities (perform separately for PMa and PMb probe intensities). For each allele of each SNP estimate the copy number using the probe intensities and the values obtained from the linear modeling of the reference samples.

Using the 100K array set, from the more than 116K SNP on the two array set, 91,908 (79.1%) were found to have a high allelic dose response as defined by a linear correlation greater than 0.8 between the target concentration and chip intensity. Among these SNPs, 51097 (55.6%) incorporated information from all 20 PM probes (10 PMa and 10 PMb), 31857 (34.6%) incorporated information from 15~19 probes, 8268 (8.9%) incorporated information from 10~14 probes, 682 (0.74%) incorporated information from 5~9 probes, 4 (0.004%) incorporated information from 3 or 4 out of 20 probes, and no SNP used less than 3 probes. This subset of 91, 908 SNPs, with an average inter-marker distance of 30.5 kb, was further evaluated for copy number estimations and significance calculations.

The performance of the methods were evaluated using a set of test samples that included 90 normal individuals, genomic DNA derived from cell lines with varying numbers of X chromosomes (1X to 5X) and several human breast cancer cell lines that harbor both low level and high level copy number alterations. None of the test samples overlapped with the 128 training samples used to establish and tune the algorithm models.

The relationship between DNA copy number and fluorescent intensity of the SNP hybridization signal was evaluated using genomic DNA derived from cell lines with a defined number of X chromosomes (1X to 5X). Amount the 91,908 selected SNPs, 1,955 map to the X chromosome. A normal 2X (NA15029) female sample was used as the reference for comparisons to the 1X, 3X, 4X, and 5X samples. The ln(PMA)+ln(PMb) for the SNPs was plotted for 1X v. 2X, 3X v. 2X, 4X v 2X and 5X v 2X. A high linear correlation among the sample pairs was observed, and only X-chromosome SNPs showed intensity profile shifts across the four panels while the autosomal SNPs remained static. A strong linear relationship was observed between the log transformed copy number and log transformed intensity (mean of ln(PMA)+ln(PMb) on X chromosome SNPs. These results show that the 100K WGSA PCR fractions maintain a nice dose response between the input template copy number and the post hybridization SNP fluorescent intensity.

Table 1 summarizes the estimation of true positive rates for detection of X chromosome changes using the 1X, 3X, 4X and 5X DNA samples along with the false positive rate of detection of autosomal SNPs deviating from the diploid state using the test set of 90 normal individuals. Values are computed for all samples at several different stages of the algorithm and at various significance thresholds. The stages of the algorithm are: single point analysis (SP), kernel smoothing with a 100 kb window after single point analysis (KS) and tree partitioning of the genome on the kernel smoothed result (TR). The results indicate that the addition of the kernel smoothing and the tree partitioning improves the true positive rate and decreases the false positive rate; only at the most stringent significance cut-off does the false positive rate exceed the expected value. Moreover, with the regression tree partition function, the algorithm defines the alterations on the X chromosome as a single region for all four samples with a very high significance. The overall copy number estimates (and significance) for the X chromosome using the 1X to 5X samples are: 1X: 0.92 ($1.99 \times 10^{-4}$), 3X: 3.21 ($8.13 \times 10^{-6}$), 4X: 4.36 ($6.15 \times 10^{-12}$) and 5X: 5.74 ($1.50 \times 10^{-16}$).

TABLE 1

| Sample and Data | Stage | p-value < $10^{-2}$ | | p-value < $10^{-4}$ | | p-value < $10^{-6}$ | | Total |
|---|---|---|---|---|---|---|---|---|
| | | Count | Percent | Count | Percent | Count | Percent | Count |
| 90 normal samples (autosomes) | SP | 409049 | 5.05% | 42182 | 0.52% | 11154 | 0.14% | 8095770 |
| | KS | 40247 | 0.497% | 3302 | 0.041% | 770 | 0.009% | 8095770 |
| | TR | 5417 | 0.067% | 506 | 0.006% | 167 | 0.002% | 8095770 |
| 1X | SP | 1441 | 73.71% | 694 | 35.50% | 286 | 14.63% | 1955 |
| | KS | 1780 | 91.05% | 714 | 36.52% | 111 | 5.68% | 1955 |
| | TR | p-value = $1.99 \times 10^{-4}$ | | | | | | 1955 |
| 3X | SP | 1271 | 65.01% | 879 | 44.96% | 603 | 30.84% | 1955 |
| | KS | 1707 | 87.31% | 1136 | 58.11% | 547 | 27.98% | 1955 |
| | TR | p-value = $8.13 \times 10^{-6}$ | | | | | | 1955 |
| 4X | SP | 1726 | 88.29% | 1523 | 77.90% | 1343 | 68.70% | 1955 |
| | KS | 1929 | 98.67% | 1861 | 95.19% | 1697 | 86.80% | 1955 |
| | TR | p-value = $6.15 \times 10^{-12}$ | | | | | | 1955 |

TABLE 1-continued

| Sample and Data | Stage | p-value < $10^{-2}$ | | p-value < $10^{-4}$ | | p-value < $10^{-6}$ | | Total Count |
|---|---|---|---|---|---|---|---|---|
| | | Count | Percent | Count | Percent | Count | Percent | |
| 5X | SP | 1884 | 96.37% | 1801 | 92.12% | 1724 | 88.18% | 1955 |
| | KS | 1950 | 99.74% | 1933 | 98.87% | 1907 | 97.54% | 1955 |
| | TR | p-value = $1.50 \times 10^{-16}$ | | | | | | 1955 |

These 90 HapMap CEPH test samples (30 trios) were used to further evaluate the accuracy of the SNP copy number estimations as well as the algorithm false positive rate (FPR). These samples were assumed to represent normal diploid genomes which do not harbor extensive genomic deletions or amplifications. Although these samples could contain copy number polymorphisms (CNP), they are relatively rare and thus were not considered in this analysis (Iafrate et al. Nat. Genet. 36:949-951, 2004; Sebat et al. Science 305:525-528, 2004). A possible explanation for a higher-than-expected false positive rate at the stringent p-value of less than $10^{-6}$ is that some false positives are not actually false positives but rather true and significant copy number polymorphisms occurring in normal people. For example, there were 167 data points identified with a significance level less than $10^{-6}$, of which 72 were derived from a common amplified region on chromosome 8 from two samples originating from the same trio, namely NA12802 (child) and NA12814 (father). The region partially overlaps with a BAC clone (RP11-9013) from 8p22 that has detected a CNP (Sebat et al. 2004) and may represent a CNP that is transmitted through generations.

There were 89,953 autosomal SNPs among the 91,908 total SNPs used for copy number analysis that were examined across the 90 individuals for a total of 8,095,770 data points (X chromosome SNPs were excluded due to copy number differences between males and females). The copy number estimation of each autosomal SNP across these 90 test samples also has relatively low variation. The mean copy number across all autosomal SNPs ranges from 1.951 to 2.032 and is similar whether using only kernel smoothing or kernel smoothing combined with regression tree. By adding the regression tree as the final partition step, the standard deviation is reduced by an average of 81.4%, and the range changes from 0.149-0.367 to 0.019-0.037. Using regression tree more regions are identified as diploid than when using kernel smoothing only, indicating an improved false positive rate when regression tree is used.

Receiver Operating Characteristic (ROC) curves were used to evaluate the overall sensitivity (true positive fraction) and specificity (true negative fraction) of different stages of the algorithm. All of the ROC curves moved steeply towards the upper left corner of the plot before leveling out across the X axis. Table 2 summarizes the area under the curves at different stages of the algorithm. Stage 1 is single point analysis: no probe selection, no intensity adjustment on fragment length and GC content; no intensity adjustment on reference mean. Stage 2 is Stage 1 plus probe selection. Stage 3 is Stage 2 plus intensity adjustment on fragment length and GC content and intensity adjustment on reference mean. Stage 4 is Stage 3 plus kernel smoothing with 100 kb window. Stage 5 is Stage 4 plus genome partitioning using the regression tree. The specificity is estimated using the 47 female samples that are a subset of the 90 normal test set samples and is restricted to the 1955X chromosome SNPs. The sensitivity is estimated on 1955X chromosome SNPs using DNA samples with 1X, 3X, 4X and 5X.

TABLE 2

Area under the ROC curve derived from different stages of the CARAT method.

| Area under ROC Curve | 1X | 3X | 4X | 5X |
|---|---|---|---|---|
| Stage 1 | 0.6240 | 0.5188 | 0.6575 | 0.7863 |
| Stage 2 | 0.6732 | 0.5384 | 0.6840 | 0.8128 |
| Stage 3 | 0.9319 | 0.8987 | 0.9546 | 0.9877 |
| Stage 4 | 0.9887 | 0.9759 | 0.9974 | 0.9995 |
| Stage 5 | 0.9999 | 0.9999 | 1.0000 | 1.0000 |

The results indicate that moderate copy number changes such as the loss of one copy or the gain of one, two, or three additional copies can be successfully detected as true positive signals while maintaining a low false-positive rate.

The most significant improvement resulted from the adjustment based on fragment length, GC content and reference mean; the AUC (Area Under the Curve) increases about 50% for the 1X, 3X and 4X samples and 21.5% for the 5X sample. The improvement from probe-selection is relatively modest, resulting in an overall increase across the samples of about 5%. Although adding the kernel smoothing in stage 4 and the tree partition in stage 5 does not substantially increase the AUC, these steps are nevertheless beneficial as they drive the AUC towards 1, ensuring high sensitivity while keeping the specificity extremely low, which is important since nearly 92K SNPs are simultaneously being examined. In the tree partitioning step (stage 5), the ROC curves are ideal for the 4X and the 5X samples, rendering an AUC of 1. For the 1X and the 3X samples, the ROC curves are not smooth but rather step-functions that achieve a 100% true positive rate with a minimum false positive rate. This occurs because for each case the regression tree step successfully identifies the variations on the X chromosome as one altered region and assigns the region a high significance score that rarely occurs in normal female samples.

A quantitative PCR (qPCR) method to measure total DNA copy number was used to independently verify algorithm-derived results. The analysis included qPCR on 69 SNPs chosen from the cancer cell line SK-BR-3, qPCR around the HER2/new region using three cancer cell lines and allele-specific TaqMan on nine SNPs across two cell lines coupled with DNA sequence analysis. All experimental results show a high correlation with estimates derived by the methods, indicating that the algorithm in combination with the Mapping 100K array set can detect chromosomal copy number changes in an accurate and quantitative manner.

The total copy number of the 69 autosomal SNPs in SK-BR-3 was determined using qPCR. The qPCR results were compared to copy number output using the methods disclosed herein as well as, dCHIP (Lin et al., *Bioinformatics*

20:1233-1240, 2004) and CNAG (Nannya et al., *Cancer Res.* 65:6071-6079, 2005). These SNPs are derived from regions of SK-BR-3 that display copy number gains and losses as well as regions with no detectable changes, covering 16 of the 22 autosomes and more than 60 different regions; 10 of the 69 SNPs have a copy number between 1.5 and 2.5, indicating no major alterations from diploidy; 14 of the 69 SNPs were excluded from CNAG because the SNPs reside on restriction fragments shorter than 500 bp and are resistant to the compensations used in CNAG. The results show that the correlation values across the three methods are not significantly different.

Table 3 shows the performance of the three methods by evaluating the sensitivity and specificity using the same 69 QPCR results. SNPs that have no copy number alterations relative to the diploid state (true negative SNPs) are defined by a QPCR derived copy number between 1.5 and 2.5. SNPs that have copy number alterations (true positive SNPs) are defined by a QPCR derived copy number less than 1.5 or greater than 2.5. There are 10 true negatives among all 69 SNPs. For the 55 SNPs that are common to CNAG, there are 9 true negatives. The calculations of sensitivity and specificity compare QPCR values to algorithm outputs in which algorithm-defined true negatives are the SNPs with an estimated copy number between 1.5 and 2.5 and algorithm-defined true positives are the SNPs with an estimated copy number less than 1.5 or greater than 2.5. In the CARAT tree-partitioning (p-value) comparison, the algorithm defined negative SNPs are those with p-value>0.005 and algorithm defined positive SNPs are those with p-value <0.005. Numerical values without parentheses are derived from comparisons using only the 55 SNPs that are in common with CNAG while the numbers inside parentheses are derived from comparisons using all 69 SNPs.

TABLE 3

| Method | Stage | Sensitivity | Specificity |
| --- | --- | --- | --- |
| CARAT | Single Point | 0.956 (0.932) | 0.444 (0.4) |
|  | 100 kb Smoothing | 0.957 (0.898) | 0.556 (0.6) |
|  | Tree Partitioning | 0.957 (0.932) | 0.778 (0.8) |
|  | Tree Partitioning (p-value) | 0.957 (0.881) | 1 (1) |
| dCHIP | Single Point | 0.783 (0.780) | 0.333 (0.4) |
|  | 10 Points Median | 0.864 (0.913) | 0.7 (0.667) |
|  | HMM | 0.978 (0.898) | 0.778 (0.8) |
| CNAG | Single Point | 0.609 | 1 |
|  | 10 points Mean | 0.522 | 1 |
|  | HMM | 0.717 | 1 |

Additional verification of DNA copy number changes detected by the algorithm was done using the highly characterized region on chromosome 17q12 harboring the ERBB2 (HER2/neu) proto-oncogene that is amplified in nearly 30% of breast cancers (Slamon et al., *Science* 244: 707-712, 1989). The genomic region near HER2/neu (genomic coordinates 38231310 to 38259791 using Genome Build 34) appears amplified in the two cancer cell lines SK-BR-3 and ZR-75-30 with moderate to very strong significance and does not appear amplified in MCF-7. This is consistent with published CGH results that show SK-BR-3 and ZR-75-30, but not MCF7, contain gains in 17q12 (Kallioniemi et al., *Proc Natl Acad Sci USA* 91:2156-2160, 1994) as well as with ERBB2-specific FISH showing amplification in SKBR3 (45 signals per cell) but not MCF7 (2.5 signals per cell) (Kallioniemi et al., *Proc Natl Acad Sci USA* 89:5321-5325, 1992). Quantitative PCR was carried out with a HER2/neu primer pair and confirmed the copy number increase in two of the three cell lines. Table 4 shows the comparisons of copy number estimated using the CARAT algorithm and by qPCR. $2^{\Delta Ct+1}$ is the theoretical estimate of total copy number using QPCR and p-val is the statistical significance of the copy number alteration. It is derived from the algorithm by comparing the target sample to a reference set of normal individuals.

TABLE 4

| HER2/NEU Region on Chr 17 | | | | | |
| --- | --- | --- | --- | --- | --- |
|  | SNP 1720794 12.48 kb proximal | | HER2/neu 38231.31- 38259.79 kb | SNP 1738376 91.64 kb distal | |
| Sample | CARAT | p-val | $2^{\Delta Ct+1}$ | CARAT | p-val |
| SK-BR-3 | 19.0 | $<10^{-20}$ | 12.4 | 19.0 | $<10^{-20}$ |
| ZR-75-30 | 25.1 | $<10^{-20}$ | 27.7 | 25.1 | $<10^{-20}$ |
| MCF-7 | 1.0 | 0.0003 | 0.8 | 2.1 | 0.567 |

While the array set does not contain SNPs within the HER2/neu gene, the SNPs which flank the locus are SNPs 1720794 and 1738376. All three cell lines show LOH in this region. MCF-7 shows no copy number reduction, illustrating how genotypic information can complement copy number information in the detection of copy-neutral LOH events. Additionally, SK-BR-3 and ZR-75-30 both show differential amplification of one allele relative to the other, resulting in allelic imbalance. Results obtained using the algorithm are also consistent with additional regional copy-number increases observed by CGH using metaphase chromosomes in MCF7 (17q22-q24; ~47.5-68.4 Mb), SKBR3 (17q24-qter; ~59.9-78.8 Mb), and ZR75-30 (17cen-q24; ~22.8-68.4 Mb) (Kallioniemi et al. 1994).

We chose 9 SNPs distributed across five different chromosomes for TaqMan analysis as an independent validation of allelic copy number information. These SNPs represent various types of alterations (allelic deletions, allelic amplifications) based on the 100K WGSA-based results. TaqMan reactions for each SNP were done with genomic DNA from SK-BR-3 and ZR-75-30 and the results are summarized in Table 5. Results for the 9 SNPs are shown in columns labeled CN_A (copy number of A allele) and CN_B (copy number of B allele). Allelic copy number estimates by TaqMan reactions are shown in parentheses. DM Call refers to the genotype call made using the Dynamic Model algorithm (DM) using a confidence rank score of 0.05. The VIC reporter dye was measuring the A allele for all SNPs except SNP 1710029 (B allele). The FAM reporter dye was measuring the B allele for all SNPs except SNP 1710029 (A allele).

TABLE 5

| | | | SK-BR-3 | | | | ZR-75-30 | | | |
| --- | --- | --- | --- | --- | --- | --- | --- | --- | --- | --- |
| SNPID | Chr | Sample Pos | P-Value | CN_A | CN_B | DM Call | P-Value | CN_A | CN_B | DM Call |
| 1724728 | 4 | 9565339 | 0.0001 | 0.89 (0.85) | 0.22 (0.0) | AA | 0.0006 | 1.77 (1.5) | 0.19 (0.02) | NC |

TABLE 5-continued

| | | | SK-BR-3 | | | | ZR-75-30 | | | |
|---|---|---|---|---|---|---|---|---|---|---|
| SNPID | Chr | Sample Pos | P-Value | CN_A | CN_B | DM Call | P-Value | CN_A | CN_B | DM Call |
| 1726250 | 8 | 89504951 | $<10^{-20}$ | 0.83 (0.97) | 14.83 (10.8) | BB | 0.141 | 0.43 (0.0) | 0.84 (1.21) | BB |
| 1700191 | 8 | 112018158 | $5.03 \times 10^{-11}$ | 0.34 (0.08) | 4.57 (5.54) | BB | $3.77 \times 10^{-19}$ | 0.81 (0.01) | 8.99 (8.93) | BB |
| 1746553 | 8 | 120342175 | $1.72 \times 10^{-20}$ | 18.45 (14.32) | 1.17 (1.43) | AA | $8.09 \times 10^{-20}$ | 10.44 (5.7) | 1.19 (0.68) | AA |
| 1710029 | 8 | 121176983 | $1.53 \times 10^{-20}$ | 19.05 (35.5) | 3.30 (1.02) | AA | $3.61 \times 10^{-20}$ | 13.60 (9.1) | 2.46 (0.77) | NC |
| 1736669 | 12 | 41456018 | 0.843 | 1.10 (1.08) | 0.90 (0.99) | NC | 0.075 | 1.68 (1.61) | 1.39 (0.03) | AA |
| 1693987 | 17 | 39301708 | $1.38 \times 10^{-16}$ | 6.20 (10.64) | 0.28 (0.28) | AA | 0.002 | 0.08 (0.0) | 1.06 (0.66) | NC |
| 1718017 | 17 | 48767363 | 0.0001 | 0.93 (0.9) | 0.15 (0.0) | NC | $5.96 \times 10^{-19}$ | 6.53 (5.58) | 2.04 (1.12) | NC |
| 1670177 | 19 | 20287003 | $1.01 \times 10^{-9}$ | 0.0 (0.0) | 0.03 (0.0) | NC | 0.310 | 0.11 (0.36) | 1.47 (0.74) | NC |

Each set of reactions also contained normal DNA samples representing AA, AB, and BB genotypes as positive controls for allele dosage. There are a total of 36 allele-specific copy number estimates when combining results for nine SNPs from the two cancer cell lines. In general, there is a good linear correlation between the allelic copy number estimates derived from WGSA and the allelic copy number using TaqMan reactions (Cor=0.87). The correlation is high, indicating an overall accurate estimation. Among the 36 data points, there are 12 examples of SNPs that have a TaqMan—determined copy number less than 0.5 for either one or both alleles, and may indicate the loss of an allele. Ten of the 12 examples also show a copy number estimation lower than 0.5 using the disclosed methods, indicating a strong consistency between the two methods.

These 12 SNPs can be further separated into four categories: (1) normal homozygous SNP (one allele present in two copies, the other allele absent), which includes SNP 1724728 and SNP 1736669 from ZR-75-30; (2) homozygous deletion (both alleles absent), which includes SNP 1670177 from SK-BR-3; (2) hemizygous deletion (one allele absent, one allele present at one copy), which includes SNPs 1724728 and 1718017 from SK-BR-3 and SNPs 1726250, 112706 and 1670177 from ZR-75-30; (4) hemizgyous deletion and one allele amplification (one allele absent and the other amplified), which includes SNP 1700191 from both samples, and SNP 1693987 from SK-BR-3. There are also 9 examples with a TaqMan-determined copy number higher than 2.5 indicating putative allelic amplification; all of these 9 examples also have a WGSA-based copy number estimation higher than 2.5. Some examples are explained by category (4) described above, while the remaining examples all appear as asymmetric amplifications (one allele remains intact, one allele amplified), including SNPs 1726250, 1746553, 1710029 from SK-BR-3 and SNPs 1710029 and 1718017 from ZR-75-30. When the TaqMan-determined total copy number is less than 1 or greater than 3, the WGSA-based method determined p-value is always very significant (<0.0001) with a single exception of SNP 112706 from ZR-75-30 (p-value 0.002).

Direct DNA sequencing was carried out on PCR amplicons from both cell lines for seven of the SNPs. SK-BR-3 showed a clear peak representing the A allele while ZR-75-30 shows a clear peak representing the B allele. Both of these base calls are consistent with the predominant allele identified by both the WGSA-based method and TaqMan. The copy number of allele B (SNP 1693987) from SK-BR-3 is below 0.5 copies based for both methods while the copy number of allele A is greater than six with both methods. The DNA sequence trace however does not detect the presence of the minor allele. In contrast, the signal from the minor allele can be detected in the case of SNP 1718017. The polymorphic nucleotide in the sense strand is either G (allele A) or T (allele B). Sequence traces using the forward primer show that in both cell lines the major allele is the A allele (G). However, ZR-75-30 also shows a smaller peak indicating the presence of allele B (T). The tracings using the reverse primer also confirm the major allele is the A allele (G) in both cell lines, and ZR-75-30 again shows a minor peak corresponding to B allele (T). There is no clear detection of the minor allele in the sequence traces from SK-BR-3 which is consistent with both CARAT (0.15 copies) and TaqMan (0 copies). In ZR-75-30, the ratio of the A allele peak height to the B allele peak height is 3.3 in the forward traces and 4.9 in the reverse traces, which are in general agreement with the allele ratios of 3.2 by CARAT and 5.0 by TaqMan. Thus the DNA sequencing results for this SNP confirm the CARAT and TaqMan results which suggested that allele B was present in at least one to two copies in ZR-75-30 but not in SKBR3.

In one aspect methods and algorithms are disclosed for estimating copy number using allele-specific probe intensity information from high density genotyping arrays. In a preferred embodiment the array includes probe sets to interrogate the genotype of more than 100,000 biallelic SNPs. Individual probes for each SNP are evaluated for the ability to support an allelic dosage response using a set of normal individuals in which the 'AA', 'AB', and 'BB' genotypes intrinsically represent zero, one and two copies of the 'B' allele and two, one, and zero copies of the 'A' allele. Probes that display a strong dosage response are employed in a regression framework to estimate allele-specific copy number. For any target sample, the sum of the copy number estimates from the two alleles is compared against the reference set to derive a significance measure of the deviation from the diploid state. Smoothing is used on the estimated copy number and its corresponding significance to further reduce the experimental and technical noise. In some embodiments regression tree analysis is applied on the smoothed result to partition the genome into regions with different copy numbers and to assign an overall significance to such changes. The method allows for allele-specific output, and when coupled with SNP genotype calls from the same array, may be used to determine the structure of genome wide alterations that contribute to allelic imbalance.

In preferred aspects, methods and computer software are disclosed that may be used in conjunction with the GeneChip® Mapping 100K Set to provide accurate copy number estimates in an allele-specific manner. The methods and algorithms makes use of the highly accurate genotypic information across a set of normal individuals to identify probes with strong allele-specific dose responses. The copy number estimation is accompanied by a significance score derived by a comparison to a reference set of normal individuals. Kernel smoothing with a Gaussian kernel and a relatively small bandwidth of 100 kb is applied on the individual estimates in an attempt to achieve a balance between resolution and noise reduction.

In a preferred embodiment, regression tree analysis is applied at the end to partition the genome into regions that share the same copy number and to assign an overall copy number and significance to regions that show alteration from the diploid state. This further reduces the random variability from SNP to SNP and increases the interpretability of the output. Although regression tree is conceptually simple, it solves the complex issue of how to define genomic regions with similar alterations. The assumption under regression tree is that different regions of the feature space have a constant outcome. With a series of recursive binary splits, it efficiently and accurately stratifies the feature space into groups such that the random deviation from the fitted constant is minimized (Hastie et al., *The Elements of Statistical Learning, Data Mining, Inference, and Prediction*. Springer, 2001). In the application of regression tree to DNA copy number analysis, the feature space is one dimensional and corresponds to the physical location on the chromosome while the outcome is the unknown copy number. The non-parametric nature of the tree method thus uncouples it from the many assumptions associated with particular distributions, which is especially appropriate for this array-platform since the behavior of probe intensity can be complex and difficult to summarize. The kernel smoothing step used for noise reduction and the tree partitioning step used for genome segmentation provide a combination that renders high performance along with simple interpretation of the output (Lai et al, *Bioinformatics* 21:3763-3770, 2005).

There are a number of alternative statistical methods that may be used to analyze array data for the purpose of copy number variation detection. Several approaches have used Hidden Markov Models (HMMs) (Sebat et al. *Science* 305: 525-528, 2004; Fridlyand et al., *Journal of Multivariate Analysis* 90:132-153, 2004; and Zhou et al. *Hum Genet* 115: 327-330, 2004). Although in general the Markov chain framework does fit genome-wide copy number variation, determination of the specific parameters in the model can depend on the patterns of variation in the samples. Thus the performance depends on how well the actual distribution of copy number variation from experimental samples such as cancer cells, which is largely unknown, agrees with the distribution hypothesized by the model. Additional approaches include change-point analysis (Fridlyand et al. *Journal of Multivariate Analysis* 90: 132-153, 2004; Olshen and Venkatraman *Proceedings of the Joint Statistical Meetings*, 2002; Olshen et al. *Biostatistics* 5: 557-572, 2004) or posterior log likelihood (Daruwala et al. *Proc Natl Acad Sci USA* 101: 16292-16297, 2004) to partition the genome into normal versus changed regions. These approaches assume that the intensity variability of probes corresponding to any region of the genome is similar. However, using WGSA and the high density arrays, there may be substantial variation in the intensities of different SNPs. This can result from differences in SNP probe sequences as well as the restriction fragment target sequences. Regression on the probe GC content and the restriction fragment length stabilize SNP variability and improves sample-to-sample comparisons. In addition, the use of a large normal reference set enables the intensity distribution on diploid genomes to be estimated at an individual SNP level, thereby improving the accuracy of the model. There is also an algorithm that uses a hierarchical clustering scheme along the chromosome to identify changes. Here the signal threshold is set by directly controlling the false discovery rate (FDR), providing a high level of confidence in the results (Wang et al. *Biostatistics* 6: 45-58, 2005). The challenge with such an approach is that a desirable FDR level can make it difficult to detect moderate changes that only span a short stretch of the genome.

As a result selection of the p-value threshold which separates significance from insignificance impacts the results and should be selected with care. If the threshold is too low, data points that do not have real copy number changes (false positives) can be included. Conversely, if the threshold is too high, data points that do have real copy number changes may be excluded. In addition, kernel smoothing across neighboring SNPs may result in the loss of single point resolution. In preferred aspects these concerns may be minimized or reduced by analyzing a larger number of SNPs, for example, more than 250,000 or more than 500,000 SNPs.

Data Analysis Methods

1. Intensity Transformation and Standardization

Figure 5:
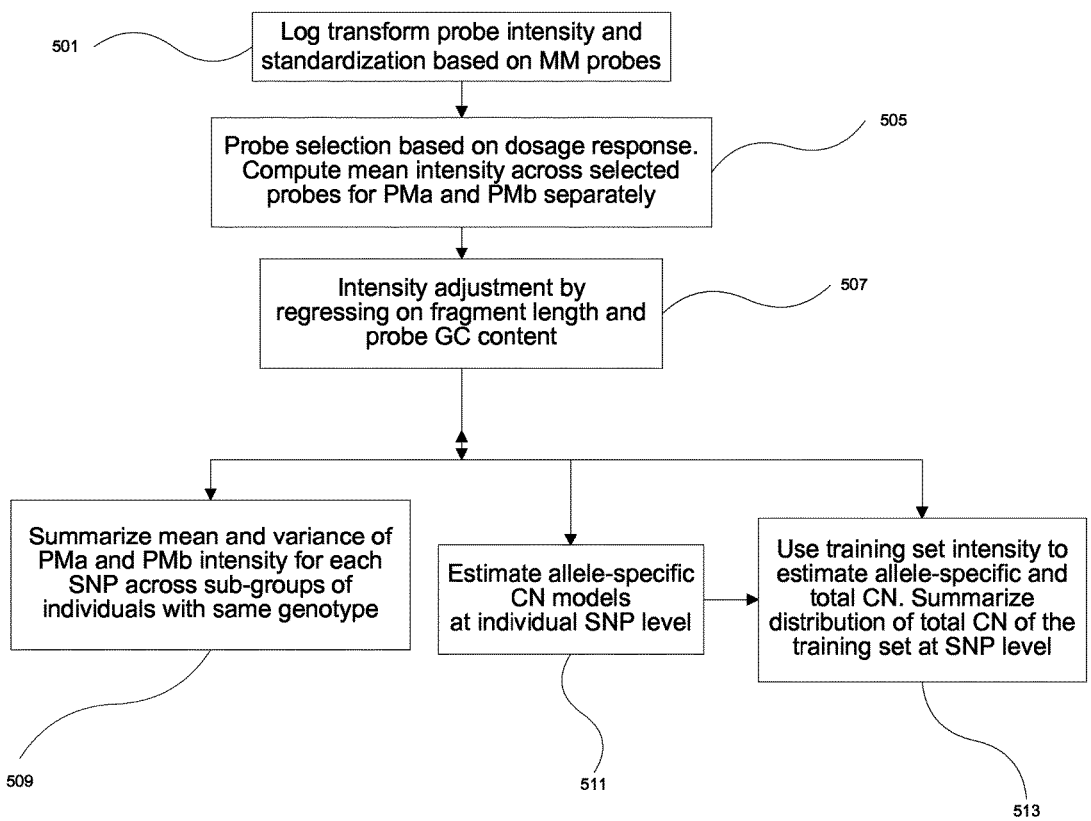
FIG. 5 shows a flowchart for a method of analyzing a training or reference set of samples.
Figure 6:
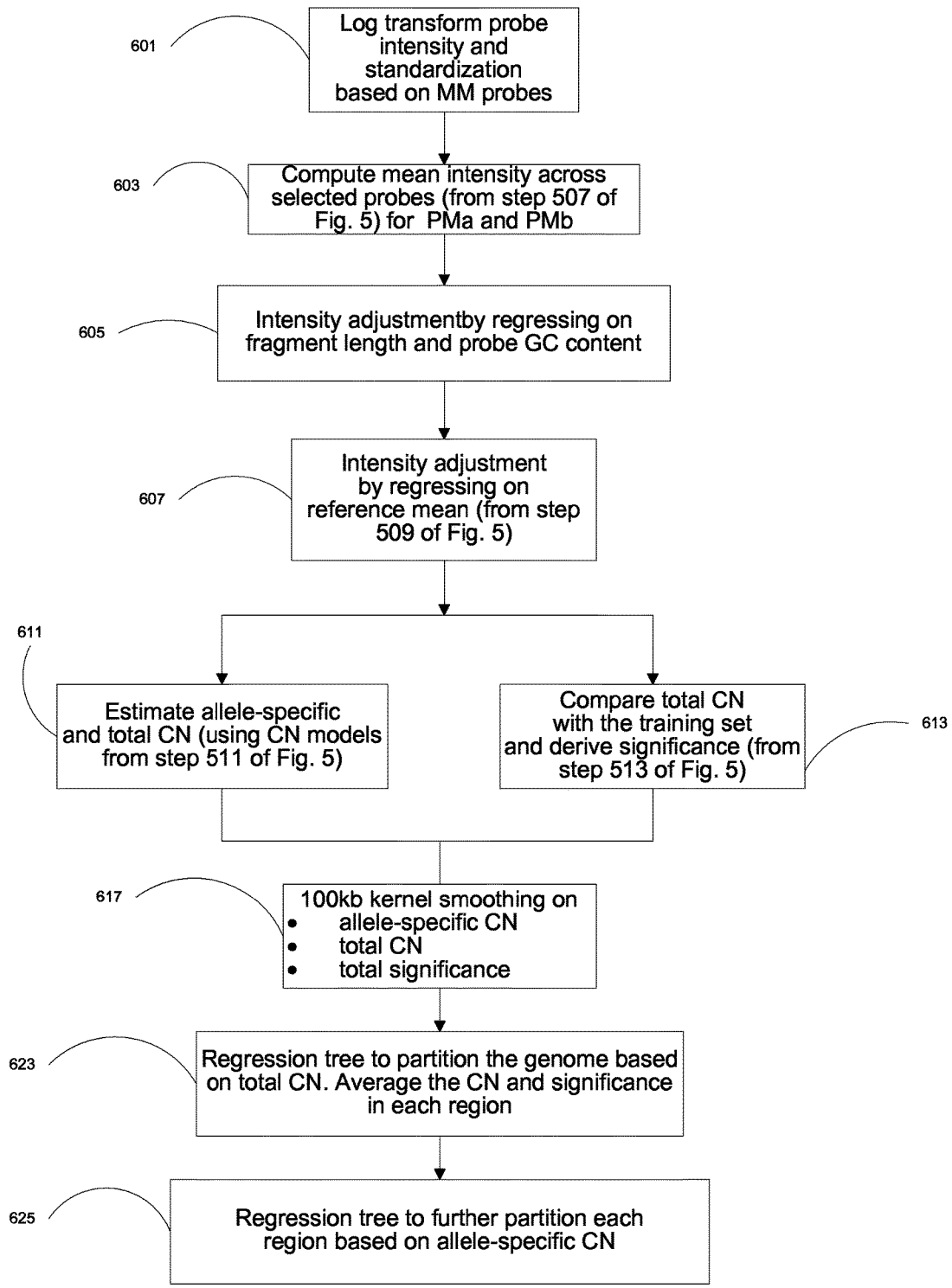
FIG. 6 shows a flowchart for analysis of a test sample with regression tree analysis for final partitioning.

In one aspect, the basic premise underlying copy number estimation is that the natural log-transformed chip intensity (following SNP-specific affinity and non-specific hybridization adjustments) is linearly related to the natural log of the DNA target copy number:

$$I_m = \alpha_{m,0} + \alpha_{m,1} \ln(\delta_m + C) + A_m + \varepsilon \qquad (1)$$

where $m=1, \ldots, M$ is the SNP index, $I_m$ is the natural log-transformed probe intensity on SNP m, $\alpha_{m,0}$ is the SNP-specific optical background, $\alpha_{m,1}$ is the scaling factor, $\delta_m$ is the non-specific hybridization, C is the DNA target concentration (i.e. copy number), $A_m$ is the affinity term determined by probe and target fragment sequences, and $\varepsilon$ is the random noise. The allele specific copy number estimation (Eq 8 and 9) is based on this fundamental assumption. The only major difference is the affinity term $A_m$ in Eq 1, which has been estimated and regressed out using a quadratic regression model with probe GC content and fragment length as the predictors (Eq 4 and 5). To better understand the details of the method, the main steps of the algorithm are summarized in FIGS. 5 and 6. The algorithm implements two rounds of standardization (Eq 2, 6, and 7). The first is applied on the natural log-transformed raw intensity (Eq 2) and establishes the comparability across samples. The second is applied prior to the copy number estimation, and realigns the target intensity according to the mean from the reference pool (Eq 6 and 7), thereby eliminating any systematic intensity shift that has not been adjusted by the previous standardization (Eq 2) or the affinity-based correction (Eq 4 and 5). This algorithm also employs a probe selection procedure (Eq 3) following the first round of standardization in which only probes that show a strong dosage response across samples (as described in Eq 1) are selected for further analysis. Kernel smoothing is applied on the estimated copy number at the level of individual SNPs to further reduce the experimental and technical noise.

Regression tree is applied on the smoothed result to partition each chromosome into regions with different copy numbers, to assign significance to each region, and to increase the interpretability of the overall results. All the parameters in the algorithm are optimized using a training set with 128 individuals. The training set (Coriell Repositories) consists of 42 African Americans, 20 Asians, 42 Caucasians and 24 samples from the polymorphism discovery panel (Collins et al., *Genome Res.* 8:1229-1231, 1998). Among them, 71 are females and 57 are males. The information from the training set including the intensity and genotype are publicly available upon request. Other training sets may also be used.

In a preferred aspect ach SNP on the genotyping array is represented by a set of unique features (probes) for each allele. Each SNP may have, for example, 20 to 80, probes for each SNP. For example, the Mapping 100K array set has 40 unique features for each SNP: 10 perfect match (PM) probes and 10 mismatch (MM) probes for both the A and B alleles. The natural log-transformation of the raw intensity is first applied at the probe level for all SNPs. After the transformation, standardization is performed based on MM probe intensities which represent background signals. This achieves a standard Gaussian distribution of the background intensity to increase the comparability across arrays. For each array with a single DNA sample, background intensity is defined as the MMa probe intensity for all SNPs with 'BB' genotype calls and the MMb probe intensity for all SNPs with 'AA' genotype calls. All PMa probes are linearly transformed such that under the same transformation the MMa probes for SNPs with 'BB' genotype calls have a variance of one and a mean of zero; all PMb probes are linearly transformed such that under the same transformation the MMb probe intensity on SNPs with 'AA' genotype calls have a variance of one and a mean of zero.

Following ln-transformation and standardization, the 20 PM probe intensities in conjunction with the genotype information is then analyzed for copy number information.

$$S_{a,lmn} = \frac{\ln(PM_{a,lmn}) - \hat{\mu}_{a,l}}{\hat{\sigma}_{a,l}} \text{ with } \hat{\mu}_{a,l} \text{ and } \hat{\sigma}_{a,l} \quad \text{(Equation 2)}$$

the sample estimation under the assumption $\ln(MM_{a,lmn} | SNPm$ is autosomal and called genotype $BB$ on sample $l) \sim N(\mu_{a,l}, \sigma_{a,l})$ $$S_{b,lmn} = \frac{\ln(PM_{b,lmn}) - \hat{\mu}_{b,l}}{\hat{\sigma}_{b,l}} \text{ with } \hat{\mu}_{b,l} \text{ and } \hat{\sigma}_{b,l} \text{ the}$$

sample estimation under the assumption $\ln(MM_{b,lmn} | SNPm$ is autosomal and called genotype $AA$ on sample $l) \sim N(\mu_{b,l}, \sigma_{b,l})$ $l=1, \ldots, L$ is the sample index: $m=1, \ldots, M$ is the SNP index; $n=1, \ldots, N$ is the probe index. $\hat{\mu}_{a,l}, \hat{\mu}_{b,l}, \hat{\sigma}_{a,l}, \hat{\sigma}_{b,l}$, are sample specific parameters; and are subject to change for any future experiments. Following natural log-transformation and standardization, the 20 PM probe intensities in conjunction with the genotype information is then analyzed for copy number information.

2. Probe Selection

PM probes which display a strong dosage response are selected for use in the algorithm. Each SNP has three possible genotypes: AA, AB and BB, which each respectively contains two, one, or zero doses of the A allele and zero, one, or two doses of the B allele. This provides an inherent positive control to examine dosage performance at the individual probe level on a SNP-by-SNP basis. Probe intensity information from a normal reference set is compared with genotypic information from the same individuals. Features with a linear correlation greater than 0.6 between the known allelic dosages based on the genotype calls and the probe intensity are selected. Intensity across selected probes is averaged and used in subsequent calculations.

$$A_m = \{n | Cor > 0.6 \text{ between } S_{a;rmn} \text{ and genotype } G_{rm} \ r = 1, \ldots, \quad (3)$$

$R$ is the reference set}

$$B_m = \{n | Cor > 0.6 \text{ between } S_{b;rmn} \text{ and genotype } G_{rm} \ r = 1, \ldots,$$

$R$ is the reference set}

$$\bar{S}_{a,lm} = \frac{\sum_{n \in A_m} S_{a,lmn}}{\#\{A_m\}}; \quad \bar{S}_{b,lm} = \frac{\sum_{n \in B_m} S_{b,lmn}}{\#\{B_m\}}$$

SNPs that do not have at least one selected probe for both PMa and PMb probe sets were excluded from further analysis. $A_m$ and $B_m$ are parameters determined by the training set and are fixed for any given training set.

3. Regression on Probe GC Content and Restriction Fragment Length

Variation of the SNP intensities can in part be explained by properties of the probe and restriction fragment sequences (Ishikawa et al, *Biochem Biophys Res Comm* 333:1309-1314, 2005 and Nannya et al., *Cancer Res.* 65:6071-6079, 2005) These properties include but are not limited to the length and GC content of the restriction fragment target, GC content of the probe sequences, and secondary structure of the probe and target sequences. An evaluation of these factors identified the GC content of the probes and the restriction fragment length as contributors to variability in probe intensities using the 100K WGSA assay. Linear regression, which included linear and square terms of both variables, may be applied to reduce the intensity variations.

$$\bar{S}_{a,l} = (\bar{S}_{a,l1}, \bar{S}_{a,l2}, \ldots, \bar{S}_{a,lm}, \ldots, \bar{S}_{a,lM}); \bar{S}_{b,l} = (\bar{S}_{b,l1}, \bar{S}_{b,l2}, \ldots, \bar{S}_{b,lm}, \ldots, \bar{S}_{b,lM})$$

$$\bar{S}_{a,l} = \beta_{a,0} + \beta_{a,1} X_{a,1} + \beta_{a,2} X_{a,1}^2 + \beta_{a,3} X_2 + \beta_{a,4} X_2^2 + \varepsilon_a$$

$$\bar{S}_{b,l} = \beta_{b,0} + \beta_{b,1} X_{b,1} + \beta_{b,2} X_{b,1}^2 + \beta_{b,3} X_2 + \beta_{b,4} X_2^2 + \varepsilon_b \quad (4)$$

$X_{a,1}$ is the probe GC content averaged across the selected PMa probes; $X_{b,1}$ is the probe GC content averaged across the selected PMb probes; and $X_2$ is the restriction fragment length. The regression coefficients are sample-specific and thus are re-estimated for each new sample.

$$\tilde{S}_{a,l} = \hat{\beta}_{a,0} + \hat{\varepsilon}_a, \tilde{S}_{b,l} = \hat{\beta}_{b,0} + \hat{\varepsilon}_b$$

$$\tilde{S}_{a,l} = (\tilde{S}_{a,l1}, \tilde{S}_{a,l2}, \ldots, \tilde{S}_{a,lm}, \ldots, \tilde{S}_{a,lM}); \tilde{S}_{b,l} = (\tilde{S}_{b,l1}, \tilde{S}_{b,l2}, \ldots, \tilde{S}_{b,lm}, \ldots, \tilde{S}_{b,lM}) \quad (5)$$

The residuals plus the constant term were used as adjusted intensity in the coming steps with the effects due to the probes and the fragment being regressed out.

4. Regression Adjustment

Following the standardization and regression on probe GC content and restriction fragment length, a further correction of systematic intensity deviations may be done by regression on the reference set mean intensities. Reference mean intensity for a given probe set (PMa or PMb) and genotype (AA, AB or BB) may be calculated for each SNP. For a given test sample, two regressions are performed in this adjustment step: one for PMa and one for PMb. In each regression, the PM intensity on the test sample across all SNPs is regressed against the average PM intensity of the reference samples that shares the same genotype as the test sample. With the estimated regression coefficients, the test sample is linearly transformed by subtracting the intercept then dividing by the slope such that after the transformation, the regression line of the test sample intensity against the average reference intensity is Y=X.

$$R_{m,AA} = \{r \mid G_{rm} = AA; r = 1, \ldots, R\}; \quad (6)$$
$$R_{m,AB} = \{r \mid G_{rm} = AB; r = 1, \ldots, R\};$$
$$R_{m,BB} = \{r \mid G_{rm} = BB; r = 1, \ldots, R\};$$
$$R_{m,all} = \{r \mid G_{rm} = AA, AB \text{ or } BB; r = 1, \ldots, R\};$$
$$\tilde{S}_{a,l} = \alpha_{a,0} + \alpha_{a,1} \times U_{a,l} + \varepsilon;$$
$$\tilde{S}_{b,l} = \alpha_{b,0} + \alpha_{b,1} \times U_{b,l} + \varepsilon$$
$$U_{a,l} = (U_{a,l1}, U_{a,l2}, \ldots, U_{a,lm}, \ldots, U_{a,lM});$$
$$U_{b,l} = (U_{b,l1}, U_{b,l2}, \ldots, U_{b,lm}, \ldots, U_{b,lM})$$

$$U_{a,lm} = \begin{cases} \frac{\sum_{r \in R_{m,AA}} \hat{S}_{a,rm}}{\#\{R_{m,AA}\}} & G_{lm} = AA \\ \frac{\sum_{r \in R_{m,AB}} \hat{S}_{a,rm}}{\#\{R_{m,AB}\}} & G_{lm} = AB \\ \frac{\sum_{r \in R_{m,BB}} \hat{S}_{a,rm}}{\#\{R_{m,BB}\}} & G_{lm} = BB \\ \frac{\sum_{r \in R_{m,all}} \hat{S}_{a,rm}}{\#\{R_{m,all}\}} & G_{lm} = \text{No call} \end{cases}$$

$$U_{b,lm} = \begin{cases} \frac{\sum_{r \in R_{m,AA}} \hat{S}_{b,rm}}{\#\{R_{m,AA}\}} & G_{lm} = AA \\ \frac{\sum_{r \in R_{m,AB}} \hat{S}_{b,rm}}{\#\{R_{m,AB}\}} & G_{lm} = AB \\ \frac{\sum_{r \in R_{m,BB}} \hat{S}_{b,rm}}{\#\{R_{m,BB}\}} & G_{lm} = BB \\ \frac{\sum_{r \in R_{m,all}} \hat{S}_{b,rm}}{\#\{R_{m,all}\}} & G_{lm} = \text{No call} \end{cases}$$

$$I_{a,l} = \frac{\tilde{S}_{a,l} - \hat{\alpha}_{a,0}}{\hat{\alpha}_{a,1}}; \quad I_{b,l} = \frac{\tilde{S}_{b,l} - \hat{\alpha}_{b,0}}{\hat{\alpha}_{b,1}} \quad (7)$$
$$I_{a,l} = (I_{a,l1}, I_{a,l2}, \ldots, I_{a,lm}, \ldots, I_{a,lM});$$
$$I_{b,l} = (I_{a,l1}, I_{b,l2}, \ldots, I_{b,lm}, \ldots, I_{b,lM})$$

Where $R_{m,AA}$, $R_{m,AB}$, $R_{m,BB}$, $R_{m,all}$ are the corresponding subsets of the reference samples whose genotypes are "AA", "AB", "BB", and the union of the three groups on SNP m, (m=1 to M); $U_{a,l}$ and $U_{b,l}$ are two vectors of the average PMa, PMb intensity across all SNPs on reference samples that share the same genotype as the target sample l; $G_{lm}$ is the genotype of test sample l on SNP m; $\tilde{S}_{a,rm}$ and $\tilde{S}_{b,rm}$ are the PMa, PMb intensity of reference sample r (r=1 to R), SNP m (m=1 to M); $\tilde{S}_{a,l}$ and $\tilde{S}_{b,l}$ are the PMa, PMb intensity of test sample l before this adjustment step; and $I_{a,l}$ and $I_{b,l}$ are the PMa, PMb intensity of test sample l after this adjustment step. The regression coefficients are sample dependent and thus are estimated for each specific sample.

5. Copy Number Prediction and Significance Calculation

A ln-ln model was used to estimate the copy number of each allele under the assumption that the natural log of the DNA target copy number has a linear relationship with the natural log-transformed intensity, where r=1, ..., R equals the reference set with an assumed diploid genome.

$$I_{a,m} = (I_{a,1m}, I_{a,2m}, \ldots, I_{a,rm}, \ldots, I_{a,RM}); I_{b,l} = (I_{b,1m}, I_{b,2m}, \ldots, I_{b,rm}, \ldots, I_{b,RM})$$

$$C_{a,m} = (C_{a,1m}, C_{a,2m}, \ldots, C_{a,rm}, \ldots, C_{a,RM}); C_{b,l} = (C_{b,1m}, C_{b,2m}, \ldots, C_{b,rm}, \ldots, C_{b,RM})$$

$$I_{a,m} = \alpha_{a0,m} + \alpha_{a1,m} \ln(C_{a,m} + \delta_{a,m}) + \varepsilon_{a,m}$$

$$I_{a,m} = \alpha_{b0,m} + \alpha_{b1,m} \ln(C_{b,m} + \delta_{b,m}) + \varepsilon_{b,m} \quad (8)$$

The parameters in the formulas were estimated using the reference set and their known genotypes. $I_{a,rm}$ and $I_{b,rm}$ are the PMa, PMb intensity of reference sample r on SNP m; $C_{a,rm}$ and $C_{b,rm}$ are the known copy numbers on the A and B alleles of reference sample r on SNP m. Since the allelic copy number can be equal to zero, for each SNP m, two small positive numbers $\delta_{a,m}$ and $\delta_{b,m}$ which represent the non-specific hybridization that account for the baseline intensity, were added. The values of $\delta_{a,m}$ and $\delta_{b,m}$ were tested over a range of 0 to 5 with 0.01 increments and the value which generated the highest linear correlation between the natural log-transformed copy number $\ln(C_{a,m}+\delta_{a,m})$ ($\ln(C_{b,m}+\delta_{b,m})$) and the natural log-transformed chip intensity $I_{a,m}$ ($I_{b,m}$) were selected. SNPs with the highest correlation value <0.8 are removed from further analysis. After $\delta_{a,m}$ and $\delta_{b,m}$ were fixed, The optical background $\alpha_{ao,m}$, $\alpha_{b0,m}$, and the scaling factor $\alpha_{a1,m}$, $\alpha_{b1,m}$, were estimated using the least square regression with the normal reference as the training set. After the estimation, the final copy number equation is:

$$\hat{C}_{a,lm} = \max\left(\exp\left(\frac{I_{a,lm} - \hat{\alpha}_{a0,m}}{\hat{\alpha}_{a1,m}}\right) - \hat{\delta}_{a,m}, 0\right) \quad (9)$$

$$\hat{C}_{b,lm} = \max\left(\exp\left(\frac{I_{b,lm} - \hat{\alpha}_{b0,m}}{\hat{\alpha}_{b1,m}}\right) - \hat{\delta}_{b,m}, 0\right)$$

All the parameters involved in the allele-specific copy number model are fixed with a given training set.

The copy number calculation is allele specific and SNP specific. The values for the two alleles can be summed to estimate the total copy number. The significance is calculated using the total copy number to identify putative amplifications and deletions. The reference samples are refitted into the ln-ln linear models and predicted total copy numbers are recorded. For a given SNP m, and a given reference sample r (r=1 to R), the predicted total copy number is:

$$\hat{C}_{t,rm} = \hat{C}_{a,rm} + \hat{C}_{b,rm} = \max\left(\exp\left(\frac{\hat{S}_{a,rm} - \hat{\alpha}_{a0,m}}{\hat{\alpha}_{a1,m}}\right) - \hat{\delta}_{a,m}, 0\right) + \max\left(\exp\left(\frac{\hat{S}_{b,rm} - \hat{\alpha}_{b0,m}}{\hat{\alpha}_{b1,m}}\right) - \hat{\delta}_{b,m}, 0\right) \quad (10)$$

For each SNP, there will be a range of variability across normal reference samples on their estimated copy numbers. This normal variation may be used to describe the reference distribution under the Gaussian assumption. Target samples are compared to this reference distribution and significance is calculated accordingly (Huang et al., *Hum. Genomics* 1:287-299, 2004).

$$\hat{C}_{t,m} = (\hat{C}_{t,1m}, \hat{C}_{t,2m}, \ldots, \hat{C}_{t,rm}, \ldots, \hat{C}_{t,Rm}) \quad (11)$$

$$\hat{C}_{t,m} \sim N(\mu_{tm}, \sigma_{tm}^2) \quad \hat{\mu}_{tm} = \frac{1}{R}\sum_{r=1}^{R} \hat{C}_{t,rm}$$

$$\hat{\sigma}_{tm} = \sqrt{\frac{1}{R-1}\sum_{r=1}^{R}(\hat{C}_{t,rm} - \hat{\mu}_{tm})^2}$$

For a given test sample lon SNP m, the total copy number estimate is:

$$\hat{C}_{t,lm} = \hat{C}_{a,lm} + \hat{C}_{b,lm} = \max\left(\exp\left(\frac{I_{a,lm} - \hat{\alpha}_{a0,m}}{\hat{\alpha}_{a1,m}}\right) - \hat{\delta}_{a,m}, 0\right) + \max\left(\exp\left(\frac{I_{b,lm} - \hat{\alpha}_{b0,m}}{\hat{\alpha}_{b1,m}}\right) - \hat{\delta}_{b,m}, 0\right) \quad (12)$$

And the significance is calculated as:

$$p_{lm} = \min\left(1 - \Phi\left(\frac{\hat{C}_{t,lm} - \hat{\mu}_{tm}}{\hat{\sigma}_{tm}}\right), \Phi\left(\frac{\hat{C}_{t,lm} - \hat{\mu}_{tm}}{\hat{\sigma}_{tm}}\right)\right) \quad (13)$$

The significance at each SNP tests whether the copy number value associated with the SNP deviates from the diploid state.

6. Define Regions with Significant Alterations

In some embodiments, prior to defining regions with significant alterations, kernel smoothing is applied to reduce the effect of outliers caused by inherent experimental error as well as the occasional true single-marker copy number variant. A bandwidth of 100 Kb with Gaussian kernel is applied on the total copy number, the significance associated with the total copy number (i.e. log 10 transformed p-values), and the allele-specific copy number. The bandwidth is fixed for all the analyses. For allele specific copy number, smoothing is applied separately on the lower copy number estimate and the higher copy number estimate at each marker in an effort to present the phased data. In order to achieve a better estimation, putative regions of LOH are first identified, defined as more than k (k=10) contiguous homozygous calls on the genome (in preferred embodiments intermittent "no calls" are allowed but not counted in k). In such regions, all markers, i.e. homozygous calls and no-calls, participate in the allele-specific smoothing. In all other regions, only markers with heterozygous genotypes are used for smoothing to prevent the underestimation of one strand and the overestimation of the other.

In the idealized case of a perfect copy number prediction on a normal diploid region of the genome, there will be heterozygous SNP genotype calls interweaved with homozygous SNP genotype calls. For heterozygous calls the lower copy number estimation and the higher copy number estimation of the two alleles will be both close to one. For homozygous calls, the lower copy number estimation for one allele will be near zero and the higher copy number estimation for the other allele will be near two. If both homozygous calls and heterozygous calls are used for allele-specific copy number smoothing, then the single point estimation on the "lower-copy-number" strand will be interweaved values close to either zero or one. After smoothing, the copy number will be lower than one. Similarly, for the alternate DNA strand, the single point estimation will contain values close to two or one and the smoothed values will therefore be higher than one. Instead, using only heterozygous calls, such under (over) estimation will be largely reduced in such normal regions. In regions with long stretches of homozygous calls, it rarely occurs randomly, but more likely caused by asymmetry between the two strands, in which case using all the markers to do the allele-specific copy number smoothing seems more appropriate.

In a preferred embodiment, a regression tree analysis method is used to further partition the genome into regions with different copy number. The regression tree method is applied to the estimated copy number (total and allele specific) and to the significance value obtained after kernel smoothing, obtained according to the methods disclosed above. Kernel smoothing is applied before regression tree analysis to reduce noise. After smoothing, regression tree (Breiman et al., *Classification and Regression Trees*, Wardsworth, 1984) is applied with the physical location of each marker as the solo predictor and natural-log transformed total copy number plus one as the outcome (adding one is done to avoid negative infinity in the case of a homozygous deletion). Log-transformation is used because heuristically the variation in intensity has been observed to increase with copy number; and log-transformation stabilizes the variance and better fits the regression tree framework. The complexity parameter is set to a small value cp=0.0001 to ensure that a complex enough partition is tested and to ensure that splits which do not increase the overall R-squared value by 0.01% are not tested. In addition, regions with equal to or less than three points are not further split. After a complex enough partition is achieved, 10-fold cross-validation and the one-standard deviation rule are applied to prune the large tree back to an appropriate size to control for over-fitting. After the final partitioning, the average (it will be a geometric average of the original copy number estimate since the regression tree is performed on the log-transformed copy number space) across a region is assigned as the copy number of that region; the significance of that region is the average of the log 10 transformed p-values (deletion uses log 10; amplification uses −log 10). Within each chromosome, regions with overall non-significant p-values (p-value >0.01) are merged with copy number information and the significance values are then updated under the assumption that they represent the same normal diploid state. For allele-specific copy number estimation, the regression-tree partition is performed in an allele-specific manner and at each region defined by the total copy number partition. The results are pruned back using cross-validation using the same approach as was carried out for the total copy number. The disclosed methods may be used for a variety of applications. The methods may be used, for example, to track cell division. During cell division DNA is replicated so at any one time some chromosomal regions will be present in extra copies. The method may be used to determine which regions of the genome have been replicated at a selected stage of cell division. The methods may be used to track cross-over hybridization and genetic rearrangements that are often associated with cancer or other disease states. The methods may be used to predict patient outcome or prognosis, to select a treatment regime for a patient or to classify a sample as being cancerous if amplification is detected by the disclosed methods. Different types of cancer may be characterized by amplification of different regions of the genome and amplification of regions to different degrees. The methods may be used to establish criteria for such classifications and for classification of samples according to established criteria. In another embodiment transcriptional profiles of samples are combined with copy number profiles to identify functional roles for genomic regions with allelic imbalances.

In a preferred embodiment the methods are used to diagnose cancers. Cancer is often associated with loss of one or more genomic regions, amplification of one or more genomic regions or rearrangement of one or more genomic regions in a tissue sample. Detection of these genomic changes may be used to diagnose cancer or to monitor the stage of a tumor. In one embodiment the amount of gene amplification may be determined in order to identify if the tissue is pre-cancerous or cancerous.

Any method of complexity reduction that results in the amplification of a predictable subset of fragments may be used to produce a reduced complexity sample. The array may be designed depending on the complexity reduction method being used and the fragments predicted to be present in the reduced complexity sample. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. patent application Ser. Nos. 09/512,300, 09/916,135, 09/920,491, 09/910,292, 10/013,598, and 10/264,945 which are incorporated herein by reference in their entireties.

Amplification methods may be optimized to amplify a subset of these fragments, for example, the fragments that are 400 to 800 basepairs. An array may be designed to detect the presence or absence of the fragments that are predicted to be amplified under a selected set of fragmentation and amplification conditions. The probes on the array may be designed to hybridize to selected regions within each fragment. One or more probes may be designed for each fragment. The probes may be optimized for hybridization using empirical criteria (see, for example, U.S. patent application Ser. No. 10/017,034 which is incorporated herein by reference in its entirety). Different arrays may be designed depending on the method used to generate the reduced complexity sample.

Prior to hybridization the fragments in the reduced complexity sample may be labeled. In another embodiment the fragments are further amplified prior to hybridization. In some embodiments the fragments are DNA and RNA is synthesized from the fragments and hybridized to an array.

In another embodiment a reduced complexity sample is hybridized to an array that is designed to interrogate all regions of a genome. Probes may be positioned uniformly throughout the genome for example 1 probe approximately every 100, 200, 1000, 2500, 10,000, or 100,000 bases.

In one embodiment the sample is hybridized directly to an array without reducing the complexity of the sample prior to hybridization. The array may be designed to detect the presence of absence of all regions of the genome using representative probes for each region of the genome or to detect selected regions of the genome.

Homozygous deletions of certain genes, for example, tumor suppressors, are known to be tumorigenic. Homozygous deletion of p53 is known to be associated with a variety of tumor types. Amplification of certain genes, for example, oncogenes, may result in overexpression of the genes which may be tumorigenic. Examples of oncogenes that are amplified in various tumors include c-myc, c-abl, c-myb, c-erbB, c-K-ras, and mdm2, see Genes VI, B. Lewin (1997) at 1144, which is incorporated herein by reference in its entirety. The method may be used to identify new homozygous deletions that are associated with cancer or another disease or phenotype. In another embodiment the method may be used to determine if an experimental sample has one or more homozygous deletions known or thought to be associated with cancer or another disease or phenotype.

Homozygous deletion of chromosomal regions are also known to cause other disorders, for example, male hypogonadism (Gromoll et al. *J Clin Endocrinol Metab* 85: 2281-2286, 2000), late onset muscular dystropyn (Pulkkinen L, et al., *Hum Mol Genet* 1996:5(10):1539-1546). Homozygous deletions have also been shown to have beneficial phenotypes such as protection against parenteral HIV-1 infection, see Kupfer et al. *AIDS*, June 18; 13(9):1025-8, 1999.

The gene-dosage techniques disclosed may be applied to measure gene copy number for a variety of diseases and applications. In addition to cancer, large genomic duplications and deletions have been found in association with diseases such as alpha-thalassaemia and Duchenne and Becker muscular dystrophies, see, for example, Armour et al. *Human Mutat* 20:325-337 (2002). The method may be used to identify a variety of chromosomal anomalies including, for example: constitutional, acquired, numerical, structural, and mosaicism. A constitutional anomaly affects the individual throughout. The chromosome error was present in the embryo. It may occur before fertilization or in the fertilized zygote. Such disorders include, chromosome inborn syndromes, such as trisomy 21, Turner syndromes, and others. Acquired anomalies affect only one organ with the other tissues being normal, such as cancer. The terms "constitutional" and "acquired" are really quite general terms, and can be applied to any persistent change encountered in clinical practice. A chromosome anomaly may also be homogenous, having all the cells studied carrying the anomaly. Normal cells may be present but not assayed. When only some cells carry the anomaly and others are normal (or carry another anomaly) the sample or individual is a mosaic. Individuals may also have numerical anomalies where one or more chromosomes are present in numbers that are different from normal. Structural changes may occur within a chromosome. The change may be balanced, if there is no loss or gain of genetic material, or unbalanced, if there is deletion and/or duplication of chromosome segment(s).

In another embodiment one or a few PM probes are used for detection of amplification or deletion. In one embodiment there are 40 probes that hybridize to the region of a SNP and are used for genotyping the SNP. The probes that work well at discrimination between specific and non-specific hybridization are used for gene dosage analysis using a genotyping array. The probes to be used may be selected by empirical performance of the individual probes. Probe behavior may be analyzed empirically to identify probes that give the most discrimination and highest signal. For Probe Specific Models see Li, C. and Wong, W.H. (2001) *Genome Biology.* 2(8): research0032.1-0032.11, Li, C. and Wong, W.H. (1998) *Proc Natl Acad Sci USA.* 98: 31-36 and Mei, R. et al. (2003) *Proc Nall Acad Sci USA.* 100: 11237-11242. In another embodiment change point analysis is used. For methods of using Change point analysis see Olshen, A. B. and Venkatraman, E. S. (2002). *Proceedings of the Joint Statistical Meetings*, Sen, A. and Srivastava, M. S. (1975). *Ann Statist.* 3 98-108 and Yao, Y-C. (1988) *Statistics & Probability Letters.* 6 181-189. In some aspects of the invention, computer software products and computer systems are provided to perform the methods (algorithms) described above. Computer software products of the invention typically include computer readable medium having computer-executable instructions for performing the logic steps of the method of the invention.

Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Computer systems of the invention typically include at least one CPU coupled to a memory. The systems are configured to store and/or execute the computerized methods described above. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

EXAMPLE

Example 1

Estimation of Copy Number Using Allele Specific Probe Intensity Data

Sample DNA was amplified using the whole genome sampling assay (WGSA). Briefly, 250 ng genomic DNA is digested in 20 µl with 10 U of either Xba I or Hind III restriction enzyme (New England Biolabs) at 37° C. for 2 hr followed by heat inactivation at 70° C. for 20 min. The digested DNA is ligated in 25 µl with 0.25 µM Xba I adaptors or Hind III adaptors and 250 units T4 DNA ligase (New England Biolabs) at 16° C. for 2 hr followed by heat inactivation at 70° C. for 20 min. DNA amplification is carried out by PCR under the following conditions: each 100 µl reaction contains 25 ng adapter-ligated genomic DNA, 1 µM primer, 300 µM dNTPs, 1 mM $MgSO_4$, 5 U Pfx polymerase (Invitrogen Corporation) in 1× Pfx Amplification buffer with 1×PCR enhancer (Invitrogen Corporation). Thermal cycling is performed at 94° C. for 3 min, followed by 30 cycles of 94° C./30 sec, 60° C./45 sec, 68° C./1 min, and a final extension at 68° C. for 7 min. PCR products are purified and concentrated with a QIAGEN mini-elute plate and then spectrophotometrically quantitated using absorbance at 260 nm. 40 µg PCR products are fragmented in 55 µl with 0.2 units DNase I (Affymetrix) at 37° C. for 30 min, followed by heat inactivation at 95° C. for 15 min. The fragmented DNA products are labeled in 70 µl reactions containing 1×TdT buffer with 105 units TdT (Promega) and 0.214 mM DLR (Affymetrix) at 37° C. for 2 hr, followed by heat inactivation at 95° C. for 15 min. DNA hybridization to the GeneChip® Human Mapping 50K Array Xba 240 and GeneChip® Human Mapping 50K Array Hind 240, washing, staining, and scanning were performed exactly as the manufacturers' instructions (Affymetrix). SNP genotype calls are made automatically using a likelihood-based model (Di et al. *Bioinformatics* 21: 1958-1963, 2005)

Total and allele-specific copy number estimations are independently evaluated for a sub-set of SNPs using quantitative PCR and TaqMan reactions with several human cancer cell lines. Quantitative PCR was performed using ABI Prism 7700 Sequence Detection System (ABI). PCR primers were designed by using Primer Express 1.5 software (ABI) and were synthesized by Operon Biotechnologies, Inc. Reactions were prepared using the SYBR-Green PCR Core Reagents kit (ABI). 69 autosomal SNPs were selected and tested. 25 µl reactions containing 25 ng genomic DNA were set up for each SNP. Normal human genomic DNA was purchased from Roche Applied Sciences. Conditions for amplification were as follows: 1 cycle of 50° C. for 2 min, followed by 1 cycle of 95° C. for 10 min, then followed by 35 cycles of 95° C. for 20 sec, 56° C. for 30 sec, and 72° C. for 30 sec. Threshold cycle numbers were obtained by using Sequence Detector v1.7a software. For all 69 SNPs, Roche human genomic DNA was used as the normal control. All reactions were done in duplicate and threshold cycle numbers were averaged. DNA amounts were measured by UV spectrophotometry and were normalized to LINE-1 elements (Wang et al. *Cancer Res* 64: 64-71, 2002). Relative quantitation was carried out using the comparative Ct method (ABI User Bulletin #2, 1997). Quantitative PCR assays for HER2/NEU were done as described except that the annealing temperature was 60° C.

Primers and probes for TaqMan analysis of 9 SNPs were ordered via the Assays-by-Design Service (ABI). TaqMan reactions contained 10 ng genomic DNA in a 25 µl reaction volume containing 1.25 U of Taq Gold DNA polymerase, 5 µM $MgCl_2$, 250 µM of dNTPs, 1 µM each of PCR primer, and both the FAM and VIC labeled TaqMan probes for the SNP at 0.1 µM final concentration. The amplification conditions consisted of an initial incubation step at 95° C. for 10 min, followed by 40 cycles at 92° C. for 15 sec, 60° C. for 1 min using an ABI Prism 7700 sequence detection system. The DNA amounts were normalized to Line-1 elements. Each SNP was tested with three normal DNA samples that represented AA, AB, and BB genotypes. We estimated the allele-specific copy number using the formula:

$$\text{copy number} = \eta_0 + \eta_1 \times 2^{\Delta Ct}$$

This linear framework fits well in general with a mean R-square value of 0.993 and standard deviation of 0.009 across the 18 linear models (9 SNPs, each 2 alleles).

Cell lines and DNA samples were as follows: All human breast cancer cell lines (MCF-7, SK-BR-3, and ZR-75-30) were obtained from American Type Culture Collection (ATCC). A normal human mammary epithelial cell line (HMEC) was obtained from Clonetics. All cells were grown under recommended culture conditions.

Genomic DNAs were isolated using QIAGEN QIAmp DNA Blood Mini Kit. DNA samples used as controls in allelic TaqMan analysis as well as DNA samples derived from cell lines containing 3X (NA04626), 4X (NA01416), and 5X (NA06061) chromosomes were purchased from NIGMS Human Genetic Cell Repository, Coriell Institute for Medical Research (Camden, N.J.).

The sensitivity and specificity of the algorithm was also characterized using DNA samples containing differing numbers of X chromosomes as well as a test set of normal individuals. Results from the algorithm show a high degree of agreement with results from alternative validation methods.

CONCLUSION

Methods of identifying changes in genomic DNA copy number are disclosed. The methods may be used to detect copy number changes in cancerous tissue compared to normal tissue. A method to identify genome wide copy number gains and losses by hybridization to a genotyping array comprising probes for more than 100,000 human SNPs is disclosed. All cited patents, patent publications and references are incorporated herein by reference for all purposes.

It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring signal intensity resulting from genomic DNA could be used. The scope of the invention should, therefore, be determined not with reference to the above description, but should instead be determined with reference to the appended claims, along with the full scope of equivalents to which such claims are entitled.

What is claimed is:

1. A method for estimating copy numbers using a high-density nucleic acid array having a plurality of allele-specific nucleic acid probes to single nucleotide polymorphisms (SNPs), and a computer system comprising at least one processor, a memory, and an interface, the method comprising:
   conducting a reference assay using a first high-density microarray genotyping assay to hybridize a plurality of fragments amplified from a reference nucleic acid sample with a plurality of allele-specific perfect match nucleic acid probes in the high-density nucleic acid array, wherein each of the plurality of allele-specific perfect match probes are complementary to individual alleles of a SNP, and wherein conducting the reference assay generates reference data by:
      measuring raw probe intensity data comprising observed intensity measurements for each probe;
      applying a log-based transformation of the raw probe intensity data for the SNPs;
      performing a standardization of the log-based transformation of the raw probe intensity data based on background intensity signals measured from a plurality of background probes to establish comparability across samples;
      identifying, using a target set of allelic copy numbers, a plurality of sets of nucleic acid probes by calculating a linear correlation between the standardized log-based transformation of the raw probe intensity data, and the copy numbers from the target set of allelic copy numbers,
      and selecting for the plurality of sets of nucleic acid probes, those sets of probes that have a linear correlation that meets or exceeds a threshold amount;
   determining and storing in the computer system a plurality of allele-specific reference models of allele-specific relationships between copy number and standardized log-based transformation of the raw probe intensity data of the selected plurality of sets of nucleic acid probes for the reference assay;
   conducting an experimental assay using the first high-density microarray genotyping assay to hybridize a plurality of fragments amplified from an experimental nucleic acid sample with the selected plurality of sets of nucleic acid probes to generate experimental data including raw experimental probe intensity data comprising observed intensity measurements for the selected plurality of sets of nucleic acid probes; and
   using the computer system to process the experimental data to genotype and determine estimated copy numbers for a plurality of alleles by applying respective allele-specific reference models corresponding to the selected plurality of sets of nucleic acid probes to respective portions of the raw experimental probe intensity data that correspond to the selected plurality of sets of nucleic acid probes.

2. The method of claim 1, wherein the threshold amount of linear correlation is 0.6.

3. The method of claim 1, further comprising determining estimated copy numbers only for SNPs that have at least one selected nucleic acid probe for each of the plurality of different alleles.

4. The method of claim 1, wherein applying a log-based transformation of the raw probe intensity data for the SNPs comprises calculating the logarithm of each of the observed intensity measurements, and wherein the observed intensity measurements are based on fluorescent intensities obtained from scanning the nucleic acid sample hybridized with the plurality of allele-specific nucleic acid probes.

5. The method of claim 1, further comprising: measuring a GC content and a restriction fragment length of each of the plurality of sets of nucleic acid probes and applying a linear regression analysis to reduce intensity measurement variability, wherein the GC content of the plurality of sets of nucleic acid probes contributes to the intensity measurement variability.

6. The method of claim 5, wherein conducting an experimental assay further comprises:
   genotyping the experimental nucleic acid sample, wherein genotyping comprises generating SNP genotype data of the experimental nucleic acid sample; and
   regressing raw experimental probe intensity data corresponding to the selected plurality of sets of nucleic acid probes against at least one mean reference intensity of the allele-specific reference model for one or more intensity measurements associated with alleles which possess a same genotype within the experimental assay as in the reference assay.

7. The method of claim 1, wherein at least one SNP is located within at least one of a plurality of genomic regions.

8. The method of claim 7, further comprising estimating a total copy number for each of the plurality of genomic regions by summing the estimated copy numbers for each of the plurality of alleles for the at least one SNP.

9. The method of claim 1, further comprising:
analyzing the estimated copy numbers for each of the plurality of alleles to calculate significance values; and
applying kernel smoothing to both the estimated copy numbers and the significance values to generate smoothed copy numbers and smoothed significance values.

10. The method of claim 1, further comprising:
fragmenting nucleic acids from the experimental nucleic acid sample with a restriction enzyme to generate nucleic acid fragments;
ligating an adaptor to the nucleic acid fragments to generate adaptor ligated fragments;
amplifying at least some of the adaptor ligated fragments to generate amplicons; and
labeling the amplicons to generate labeled amplicons, wherein at least one of the labeled amplicons is hybridized to the high density nucleic acid array.

11. The method of claim 1, wherein the high-density nucleic acid array comprises a plurality of perfect match probes for a first allele of a single nucleotide polymorphism (SNP), a plurality of perfect match probes for a second allele of the SNP, a plurality of mismatch probes for the first allele of the SNP, and a plurality of mismatch probes for the second allele of the SNP.

12. The method of claim 1, wherein the reference nucleic acid sample comprises at least one of normal samples without copy number changes and tumor samples with copy number changes.

13. The method of claim 1, wherein conducting the reference and experimental assays generates and applies allele-specific reference models for genotypes of more than 10,000, more than 100,000, or more than 500,000 SNPs in a single experiment.

14. A method for estimating copy numbers using a high-density nucleic acid array having a plurality of allele-specific nucleic acid probes to single nucleotide polymorphisms (SNPs), and a computer system comprising at least one processor, a memory, and an interface, the method comprising:
conducting an experimental assay using a first high-density microarray genotyping assay to hybridize a plurality of fragments amplified from an experimental nucleic acid sample with the selected plurality of sets of nucleic acid probes to generate experimental data including experimental probe intensity data comprising observed intensity measurements of hybridization for the selected plurality of sets of nucleic acid probes; and
using the computer system to process the experimental data to genotype and determine estimated copy numbers for a plurality of alleles by applying respective allele-specific reference models of the selected plurality of sets of nucleic acid probes to respective portions of the raw experimental probe intensity data that correspond to the selected plurality of sets of nucleic acid probes;
wherein the respective allele-specific reference models are stored in the computer system and are obtained by:
conducting the reference assay using the first high-density microarray genotyping assay to hybridize a plurality of fragments amplified from a reference nucleic acid sample with a plurality of allele-specific perfect match nucleic acid probes in the high-density nucleic acid array, wherein conducting the reference assay generates reference data by:
measuring raw probe intensity data comprising observed intensity measurements for each probe;
applying a log-based transformation of the raw probe intensity data for the SNPs;
performing a standardization of the log-based transformation of the raw probe intensity data based on background intensity signals measured from a plurality of background probes to establish comparability across samples;
identifying, using a target set of allelic copy numbers, the plurality of sets of nucleic acid probes by calculating a linear correlation between the standardized log-based transformation of the raw probe intensity data, and the known copy numbers from the target set of allelic copy numbers, and
selecting for the plurality of sets of nucleic acid probes, those sets of probes that have a linear correlation that meets or exceeds a threshold amount; and
determining and storing in the computer system the plurality of allele-specific reference models of allele-specific relationships between copy number and standardized log-based transformation of the raw probe intensity data of the selected plurality of sets of nucleic acid probes for the reference assay.

* * * * *